(12) United States Patent
Yonemura et al.

(10) Patent No.: US 6,562,041 B1
(45) Date of Patent: May 13, 2003

(54) APPARATUS AND METHOD FOR SPINAL STABILIZATION

(75) Inventors: Kenneth S. Yonemura, Seattle, WA (US); Douglas W. Kohrs, Edina, MN (US)

(73) Assignee: Sulzer Spine-Tech Inc., Minneapolis, MN (US)

( * ) Notice: Subject to any disclaimer, the term of this patent is extended or adjusted under 35 U.S.C. 154(b) by 357 days.

(21) Appl. No.: 09/717,531

(22) Filed: Nov. 21, 2000

Related U.S. Application Data

(60) Continuation of application No. 09/364,127, filed on Jul. 30, 1999, now Pat. No. 6,156,040, which is a division of application No. 08/921,001, filed on Aug. 29, 1997, now Pat. No. 6,086,595.

(51) Int. Cl.$^7$ .......................... A61B 17/56; A61B 17/58; A61F 2/30
(52) U.S. Cl. ............................................ 606/61; 606/99
(58) Field of Search .............................. 606/61, 60, 90, 606/99, 100; 623/17; 128/898

(56) References Cited

U.S. PATENT DOCUMENTS

| | | |
|---|---|---|
| 3,486,505 A | 12/1969 | Morrison |
| 3,848,601 A | 11/1974 | Ma et al. |
| 3,875,595 A | 4/1975 | Froning |
| 4,341,206 A | 7/1982 | Perrett et al. |
| 4,834,757 A | 5/1989 | Brantigan |
| 4,877,020 A | 10/1989 | Vich |
| 4,878,915 A | 11/1989 | Brantigan |
| 4,961,740 A | 10/1990 | Ray et al. |
| 5,015,247 A | 5/1991 | Michelson |
| 5,026,373 A | 6/1991 | Ray et al. |
| 5,055,104 A | 10/1991 | Ray |
| 5,484,437 A | 1/1996 | Michelson |
| 5,489,307 A | 2/1996 | Kuslich et al. |

(List continued on next page.)

FOREIGN PATENT DOCUMENTS

| | | |
|---|---|---|
| DE | 3505567 A1 | 6/1986 |
| EP | 0 260 044 A1 | 3/1988 |
| EP | 0 796 593 A2 | 9/1997 |
| FR | 78 19240 | 2/1980 |
| SU | 759096 | 8/1980 |
| WO | WO 91/06261 | 5/1991 |
| WO | WO 94/28824 | 12/1994 |
| WO | WO 96/27321 | 9/1996 |
| WO | WO 96/27345 | 9/1996 |
| WO | WO 98/17208 | 4/1998 |

OTHER PUBLICATIONS

Declaration of Douglas Kohrs, filed in Applicants' related application Ser. No. 08/015,863.
Declaration of Paul M Sand (Apr. 22, 1999).
Posterior Lumbar Interbody Fusion by Paul Lin (©1982), pp. 114–124.
Spine: State of the Art Review, vol. 6, No. 1, Jan., 1992, pp. 175–200.
Sofamor Danek Brochure: "Surgical Technique Using Bone Dowel Instrumentation".
Sulzer Spine—Tech Brochure: Anterior, 4021 Tooth Tube Surgical Technique, BAK™ Interbody Fusion System.

*Primary Examiner*—John J. Calvert
*Assistant Examiner*—Robert H Muromoto, Jr.
(74) *Attorney, Agent, or Firm*—Merchant & Gould P.C.

(57) ABSTRACT

A surgical method and apparatus for implanting a spinal fusion implant includes a rigid centering guide having a distal end sized to be inserted into the disc space with the guide extending along a longitudinal axis from a distal end to a proximal end. The guide includes a first external guide surface which extends at least partially between the distal end and the proximal end. The external guide surface is shaped complimentary to an external guided surface of a drill guide. The external guide surface and the guided surface are nested such that the guided surface slides against the external guide surface along a path of travel parallel to the longitudinal axis.

20 Claims, 18 Drawing Sheets

U.S. PATENT DOCUMENTS

| | | |
|---|---|---|
| 5,489,308 A | 2/1996 | Kuslich et al. |
| 5,505,732 A | 4/1996 | Michelson |
| 5,571,109 A | 11/1996 | Bertagnoli |
| 5,609,636 A | 3/1997 | Kohrs et al. |
| 5,653,761 A | 8/1997 | Pisharodi |
| 5,669,909 A | 9/1997 | Zdeblick et al. |
| 5,700,291 A | 12/1997 | Kuslich et al. |
| 5,720,748 A | 2/1998 | Kuslich et al. |
| 5,741,253 A | 4/1998 | Michelson |
| 5,766,252 A | 6/1998 | Henry et al. |
| D397,436 S | 8/1998 | Michelson |
| 5,797,909 A | 8/1998 | Michelson |
| RE36,020 E | 12/1998 | Moore et al. |

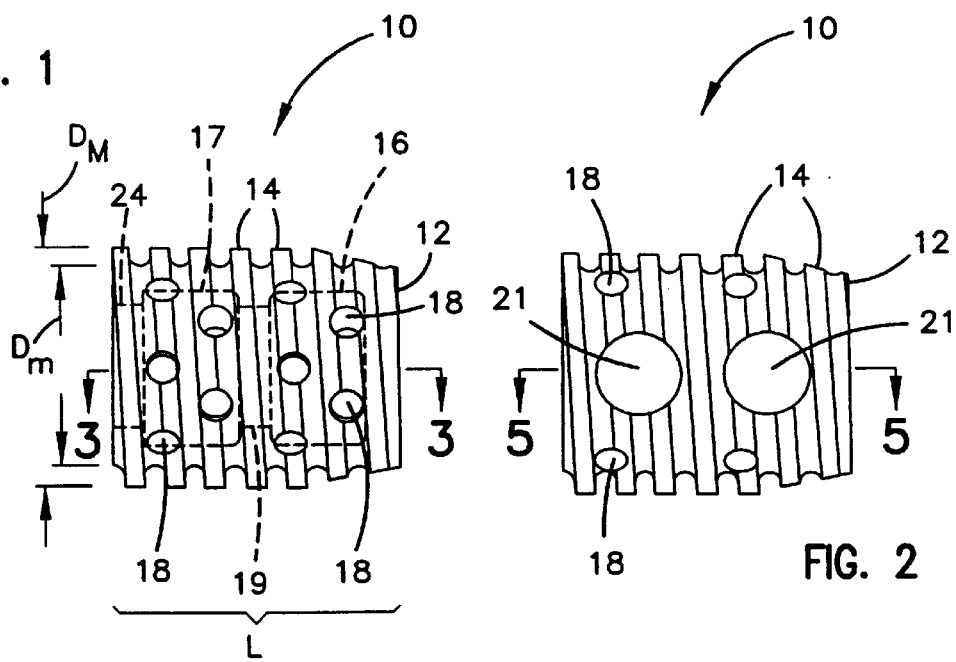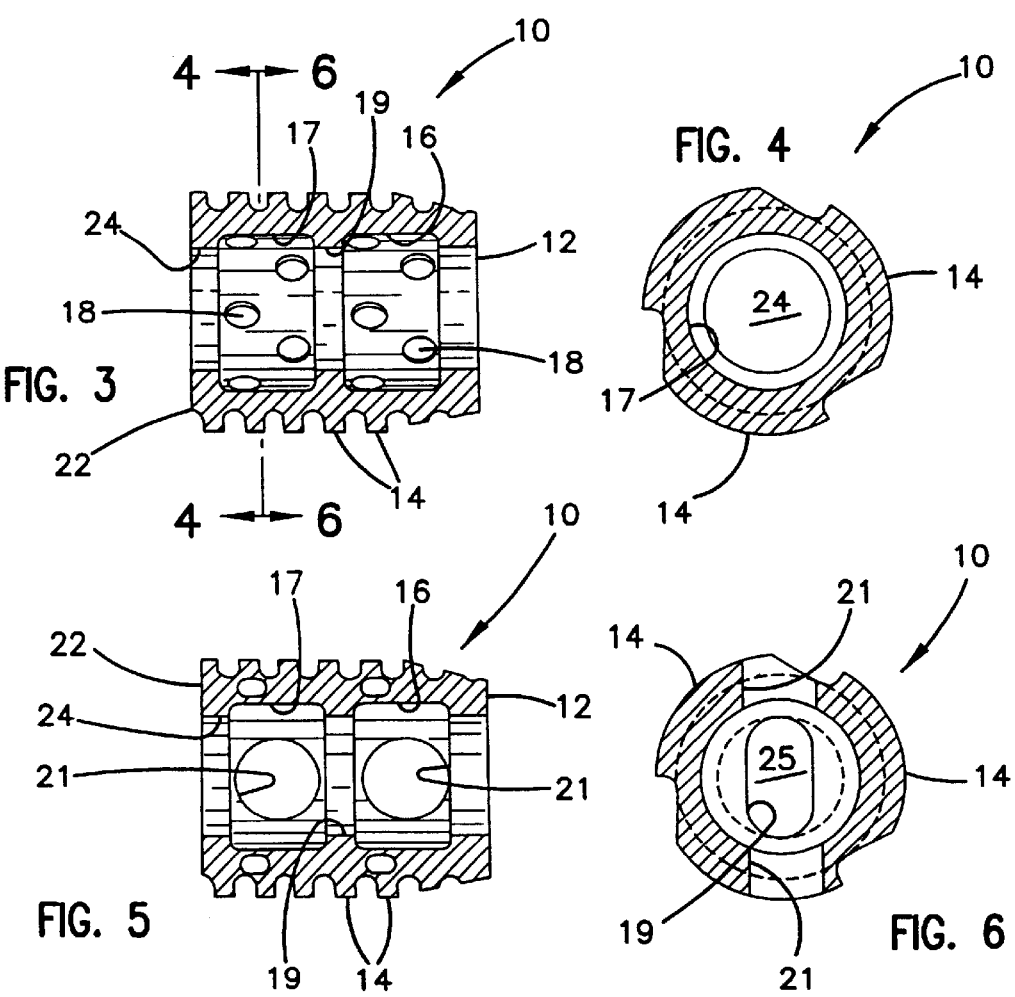

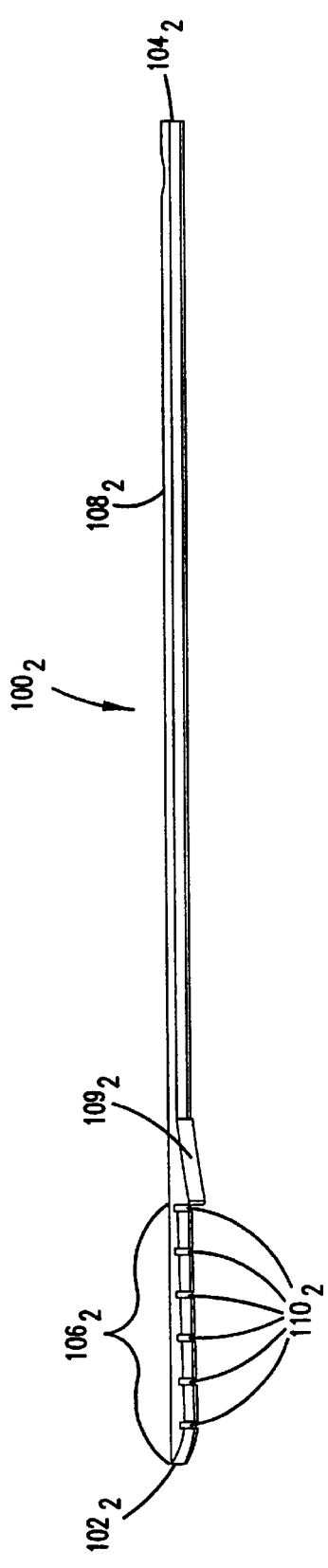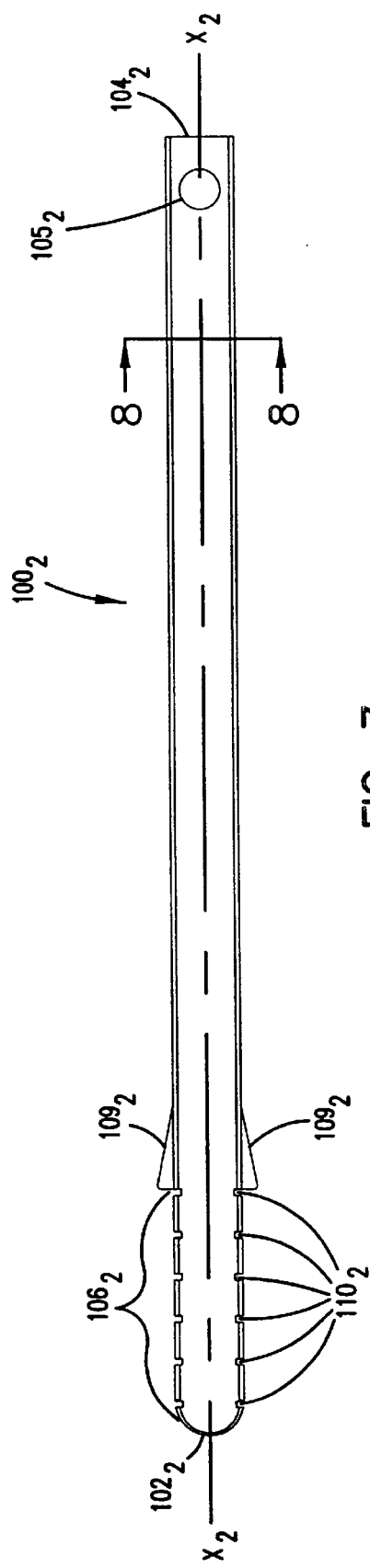
FIG. 9
FIG. 7

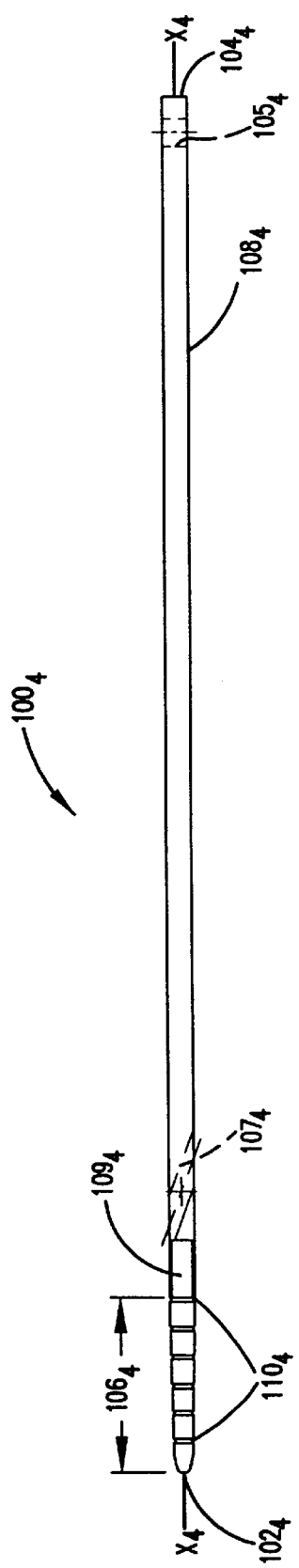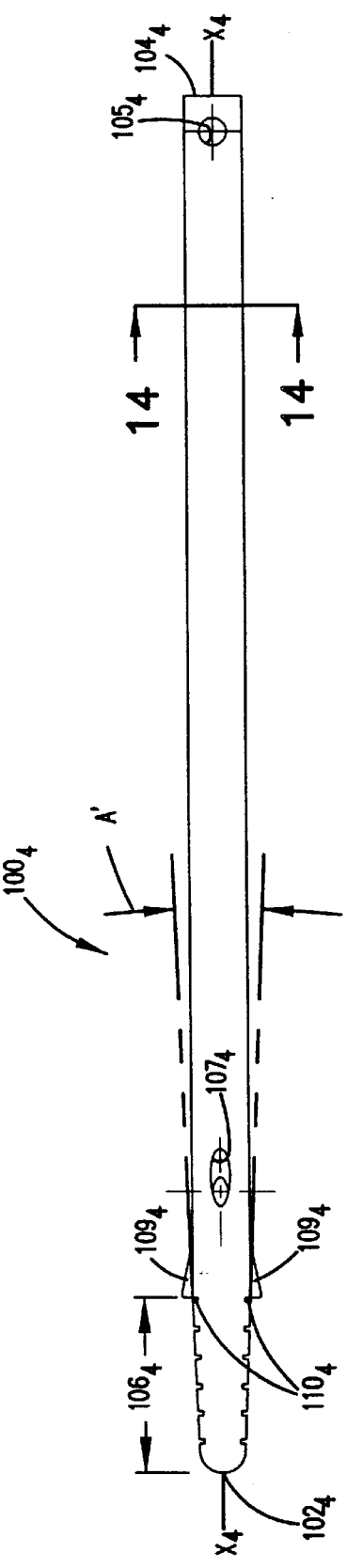
FIG. 15
FIG. 13

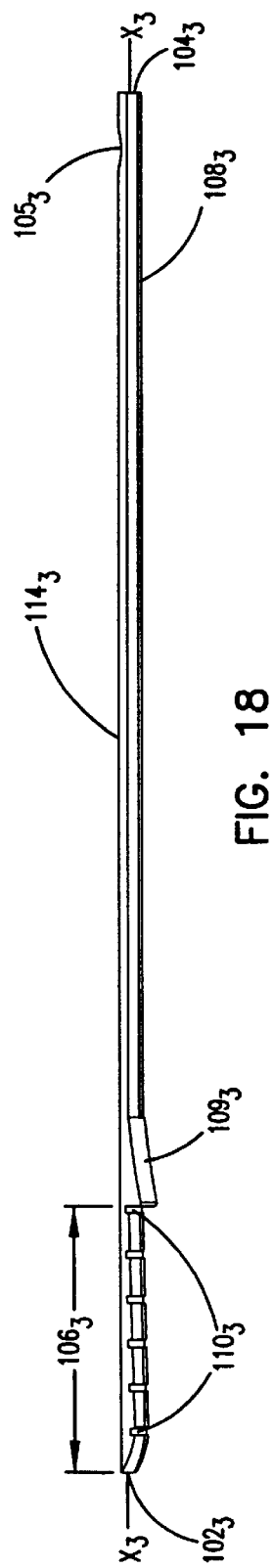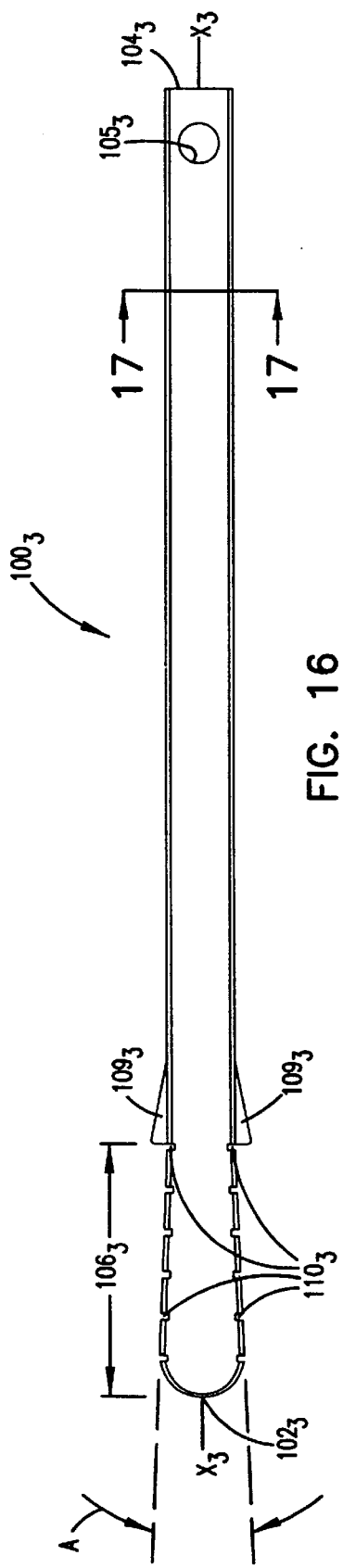
FIG. 18
FIG. 16

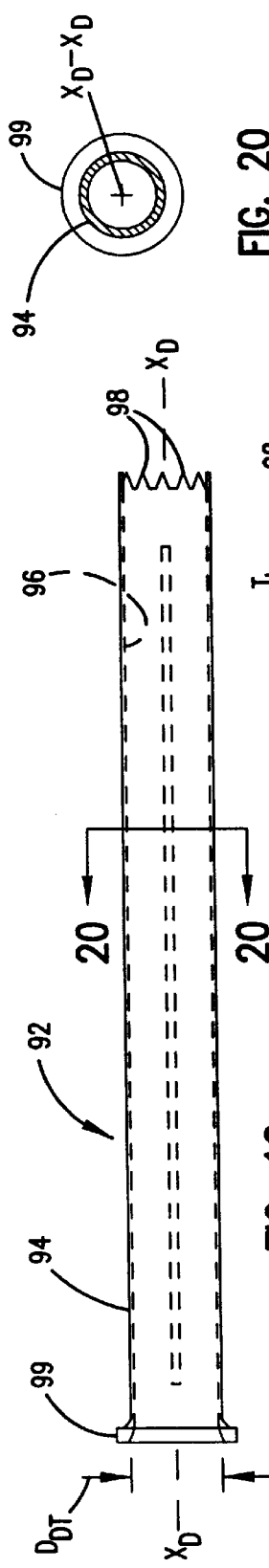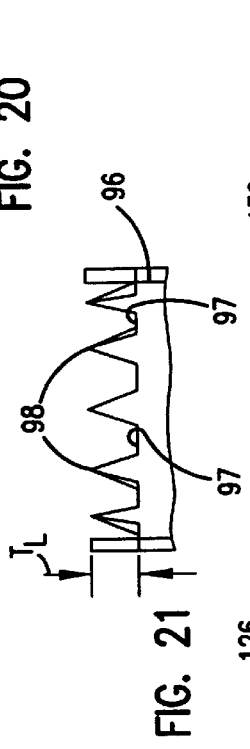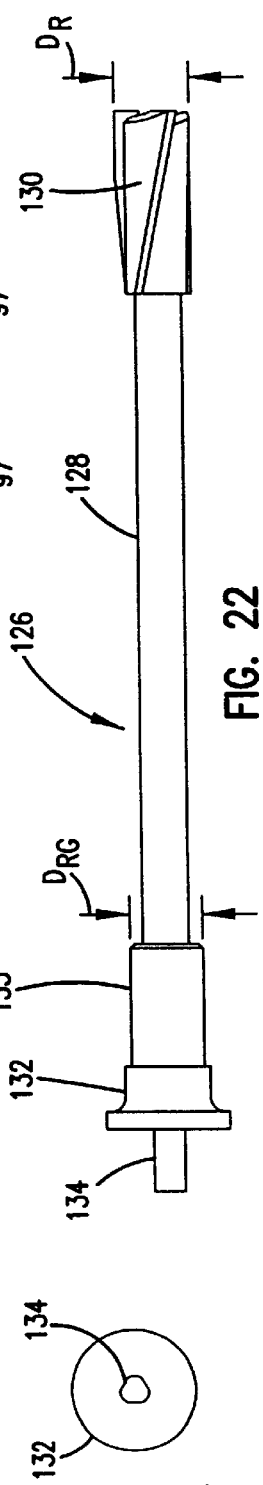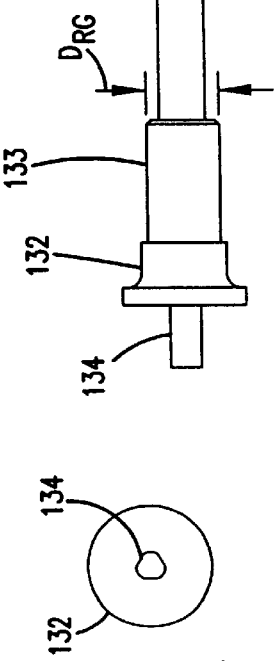
FIG. 19
FIG. 20
FIG. 21
FIG. 22
FIG. 23
FIG. 24
FIG. 25

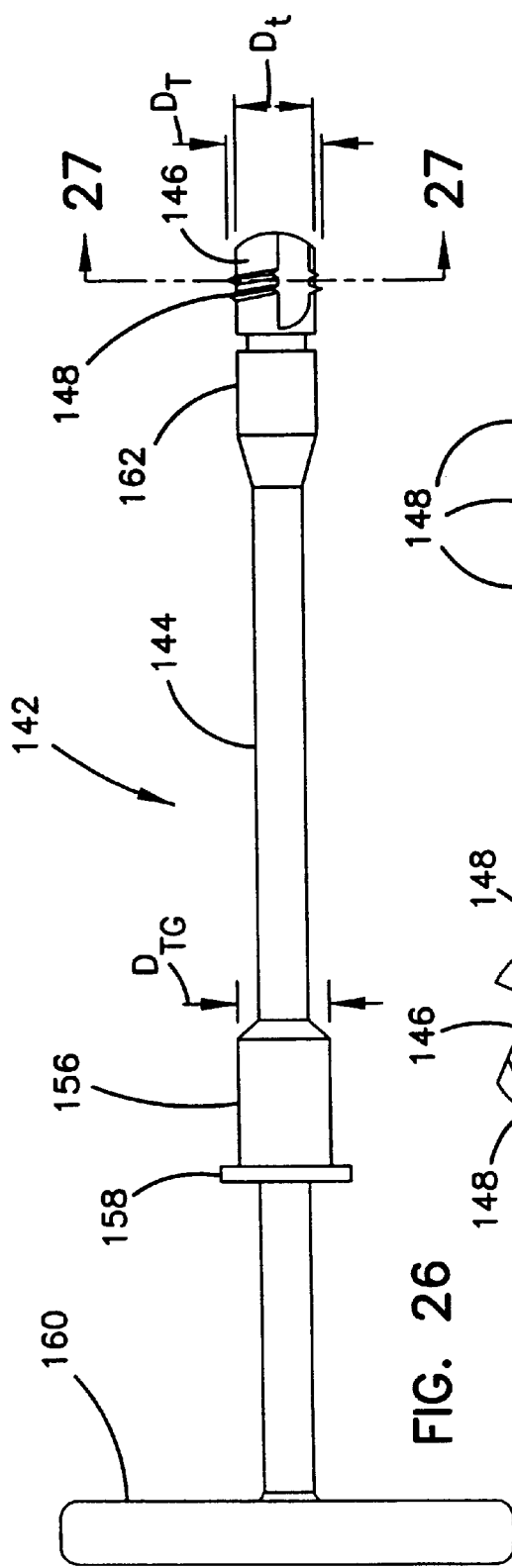
FIG. 26
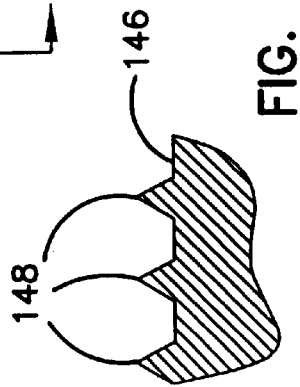
FIG. 27
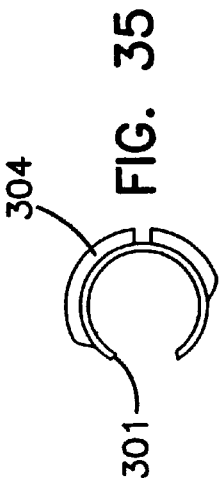
FIG. 28
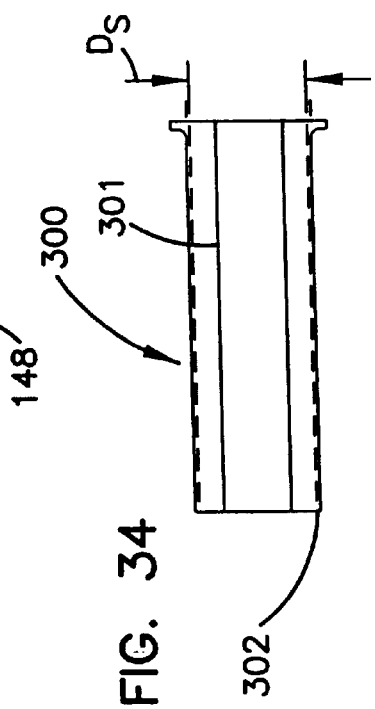
FIG. 34
FIG. 35

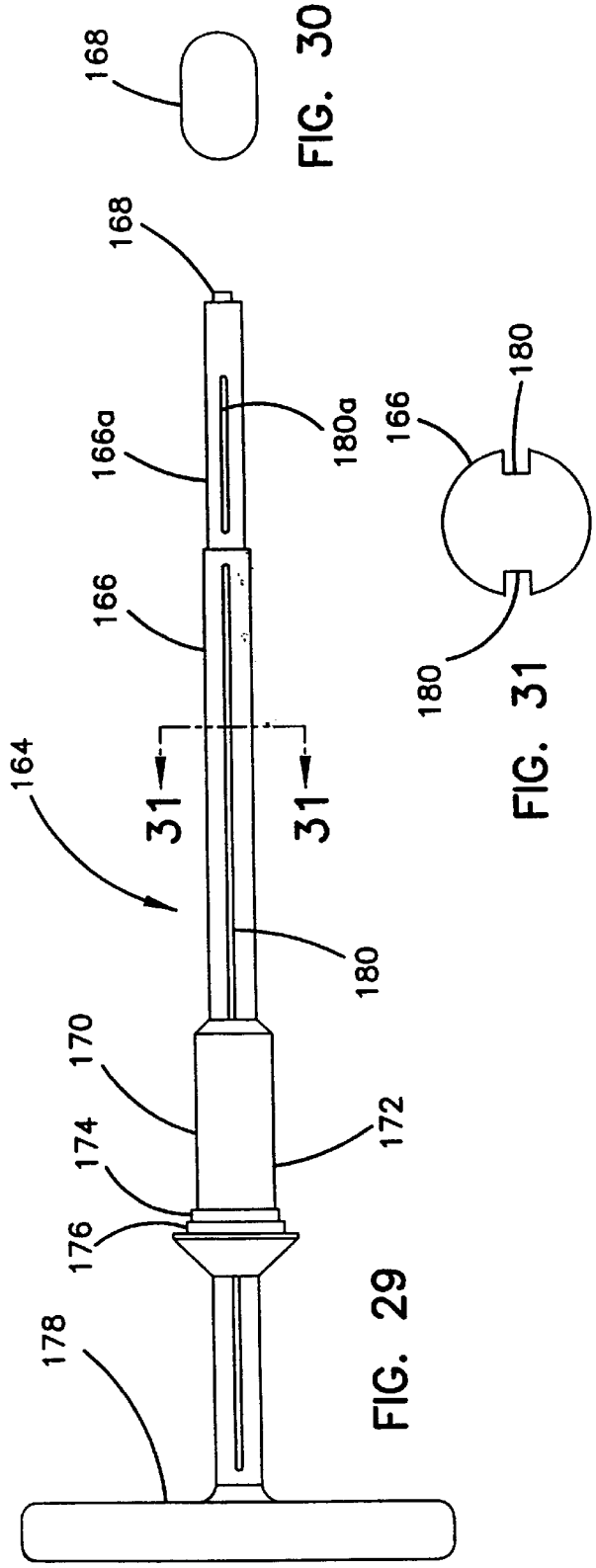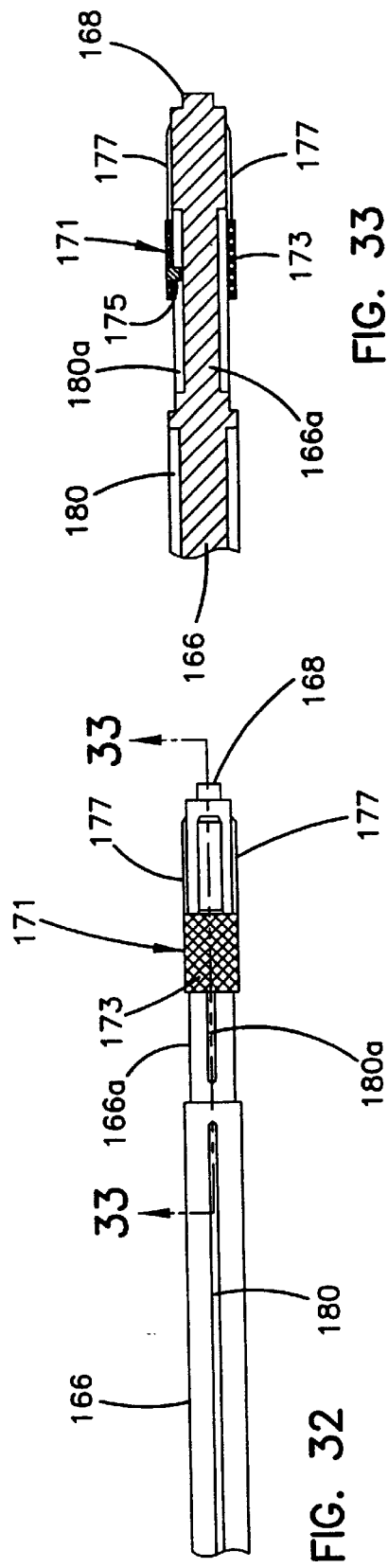

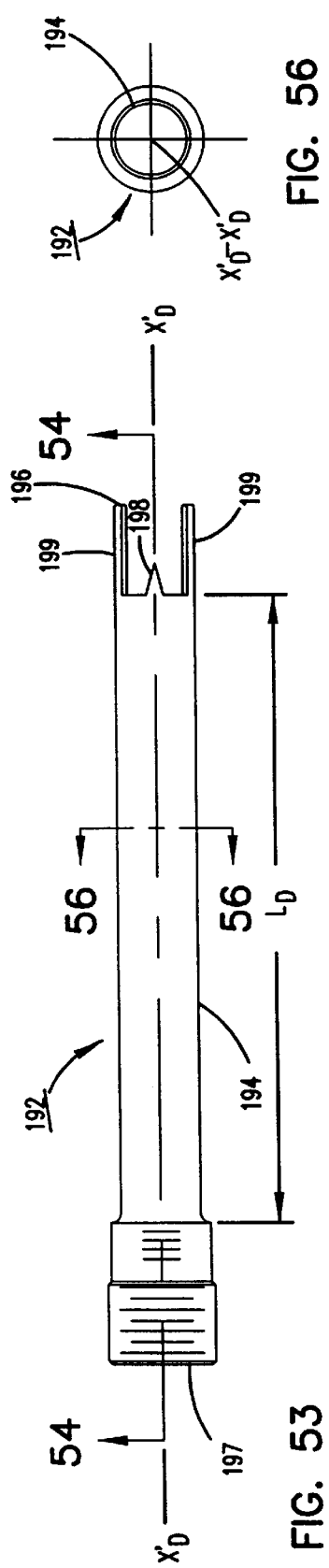
FIG. 53
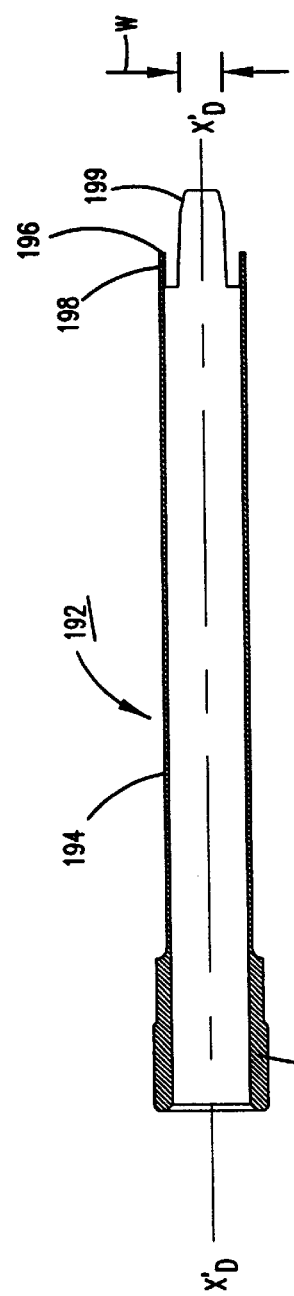
FIG. 54
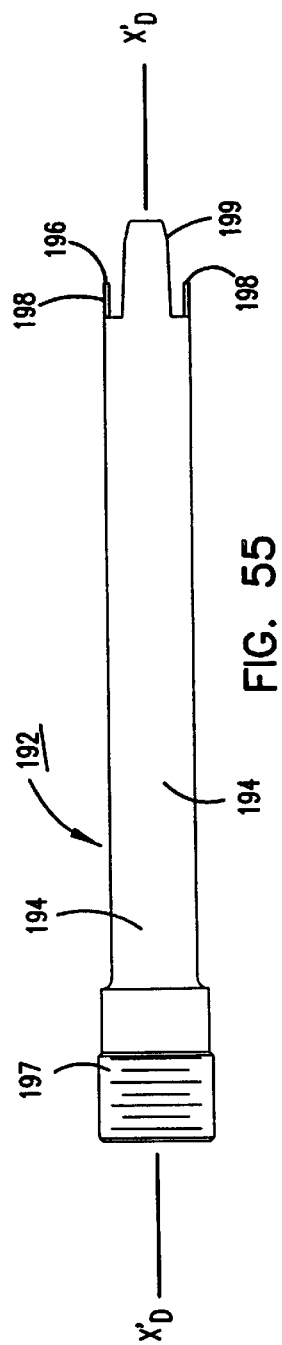
FIG. 55
FIG. 56

APPARATUS AND METHOD FOR SPINAL STABILIZATION

CROSS-REFERENCE TO RELATED APPLICATIONS

The present application is a continuation of U.S. Ser. No. 09/364,127 filed Jul. 30, 1999, U.S. Pat. No. 6,156,040, which is a divisional of U.S. Ser. No. 08/921,001, filed Aug. 29, 1997, now U.S. Pat. No. 6,086,595, the entire disclosures of which are incorporated herein by reference.

I. BACKGROUND OF THE INVENTION

1. Field of the Invention

This invention pertains to spinal stabilization surgical procedures and apparatus for performing such procedures. More particularly, this invention pertains to an apparatus and method for implanting a fusion spinal implant between two vertebrae.

2. Description of the Prior Art

Chronic back problems cause pain and disability for a large segment of the population. In many cases, chronic back problems are attributed to relative movement between vertebrae in the spine.

Orthopedic surgery includes procedures to stabilize vertebrae. Common stabilization techniques include fusing the vertebrae together.

Recently, spinal implants have been developed to facilitate successful fusion of vertebrae. In such procedures, a bore is formed between opposing vertebrae to be fused. An implant, commonly containing bone growth-inducing material such as harvested bone chips, is placed within the bore.

In order to enhance the successful procedure, a bore should be formed centrally between the vertebrae such that the bore cuts equally into both vertebrae. Also, from time to time, it is desirable to place two implants within the same disc space. In such procedures, it is desirable that the vertebrae be spaced apart by a minimum spacing sufficient to prevent the implants from contacting one another during the implanting procedure. In the prior art, numerous methods have been disclosed for performing spinal stabilization procedures.

A spinal implant and stabilization procedure is taught in U.S. Pat. Nos. 5,015,247 and 5,484,437 both to Michaelson, dated May 14, 1991 and Jan. 16, 1996, respectively. That patent teaches a threaded spinal implant as well as a method of implantation including certain tools to form a bore into which the implant is threaded. An implant and surgical method are also shown in U.S. Pat. No. 4,961,740 to Ray, et al., dated Oct. 9, 1990, as well as U.S. Pat. No. 5,026,373 to Ray, et al., dated Jun. 25, 1991. The latter patent teaches preparing a bore for the implant by drilling over a pilot rod.

In addition to cylindrical threaded implants such as those shown in U.S. Pat. No. 5,015,247, implants may take on different geometries, including non-cylindrical implants such as those shown in U.S. Pat. No. 5,609,636 dated Mar. 11, 1997. Also, conical implants have been suggested, where the conical implants have a conical angle approximating a desirable lordosis between the opposing vertebrae.

In surgical procedures involving implants, it is desirable that the surgical procedure be performed accurately to ensure central positioning of the implant within the disc space between the opposing vertebrae. U.S. Pat. No. 5,489,307 to Kuslich, et al., dated Feb. 6, 1996, teaches a plurality of instruments and a surgical method for preparing a bore for receiving an implant. That procedure results in accurately positioning an implant centrally between the opposing vertebrae while avoiding certain disadvantages with other prior art techniques as discussed more fully in the '307 patent. Unfortunately, the method and procedure of the '307 patent requires a large number of instruments which must be accurately selected and manipulated.throughout the procedure. It is an object of the present invention to provide an apparatus and method for performing spinal stabilization using a reduced number of instruments in order to simplify the procedure without sacrificing the accuracy achieved with the procedure of the '307 patent. Furthermore, it is an object of the present invention to provide a surgical procedure that can be performed posteriorly, anteriorly, laterally, or as a laparoscopic procedure.

II. SUMMARY OF THE INVENTION

According to the preferred embodiment of the present invention, an apparatus and method are disclosed for implanting a spinal fusion implant into a disc space separating a first vertebra and a second vertebra. The method comprises inserting a distal end of a rigid centering guide into the disc space. The guide extends along a longitudinal axis from a distal to a proximal end. The guide has a first external guide surface with a predetermined geometry. A drill guide is placed against the centering guide. The drill guide is adapted to axially guide a drill. The drill guide has an external guided surface which is shaped complementary to the external guide surface of the centering guide. The external guide surface and the guided surface are mutually nested with the guided surface sliding against the external guide surface along a path of travel parallel to the longitudinal axis of the centering guide. The drill guide is slid toward the vertebrae with the guide surface and the guided surface maintaining movement of the drill guide along the desired path of travel.

III. BRIEF DESCRIPTION OF THE DRAWINGS

FIG. 1 is a side elevation view of a prior art implant for use with the method of the present invention;

FIG. 2 is a view of the implant of FIG. 1 with the implant rotated 90° about its axis;

FIG. 3 is a View taken along line 3—3 of FIG. 1;

FIG. 4 is a view taken along line 4—4 of FIG. 3;

FIG. 5 is a view taken along line 5—5 of FIG. 2;

FIG. 6 is a view taken along line 6—6 of FIG. 3;

FIG. 7 is a side elevation of a first embodiment of a centering guide according to the present invention for use in a posterior approach and without a lordotic distal end;

FIG. 9 is a top plan view of the centering guide of FIG. 7;

FIG. 13 is a side elevation view of a third embodiment of a centering guide according to the present invention for use in an anterior approach and with a lordotic distal end;

FIG. 15 is a top plan view of the centering guide of FIG. 13;

FIG. 16 is a side elevation view of a fourth embodiment of the centering guide according to the present invention for use in a posterior approach and with a lordotic distal end;

FIG. 18 is a top plan view of the centering guide of FIG. 16;

FIG. 19 is a side elevation tube of a prior art drill tube for use with the present invention;

FIG. 20 is a view taken along line 21—21 of FIG. 19;

FIG. 21 is an enlarged side elevation view of a distal end of the drill tube of FIG. 19;

FIG. 22 is a side elevation view of a prior art boring tool for use with the present invention;

FIG. 23 is an elevation view of a proximal end of the boring tool of FIG. 22;

FIG. 24 is an enlarged view of a boring head of the boring tool of FIG. 22;

FIG. 25 is an end elevation view of a distal end of the boring head of FIG. 24;

FIG. 26 is a side elevation view of a prior art tap for use with the present invention;

FIG. 27 is a view taken along line 27—27 of FIG. 26;

FIG. 28 is an enlarged sectional view of threaded cutting teeth on the tool of FIG. 26;

FIG. 29 is a side elevation view of an implant driver for use with the present invention;

FIG. 30 is an end view of a hub on a distal end of the tool of FIG. 29;

FIG. 31 is a view taken along line 31—31 of FIG. 29;

FIG. 32 is a side elevation view of a shaft of a tool of FIG. 29 showing an attachment collet;

FIG. 33 is a cross sectional view of FIG. 32 taken along line 33—33;

FIG. 34 is a side elevation view of a protective sleeve for use on the drill tube of FIG. 19;

FIG. 35 is an end elevation view of the sleeve of FIG. 34;

FIG. 53 is a side elevation view of an alternative embodiment of a drill tube for use with the centering guide of the present invention;

FIG. 54 is a view taken along line 54—54 of FIG. 53;

FIG. 55 is the view of FIG. 53 with drill tube rotated 90° about its longitudinal axis; and FIG. 56 is a view taken along line 56—56 of FIG. 53.

IV. DESCRIPTION OF THE PREFERRED EMBODIMENT

A. Implant

Figure 8:
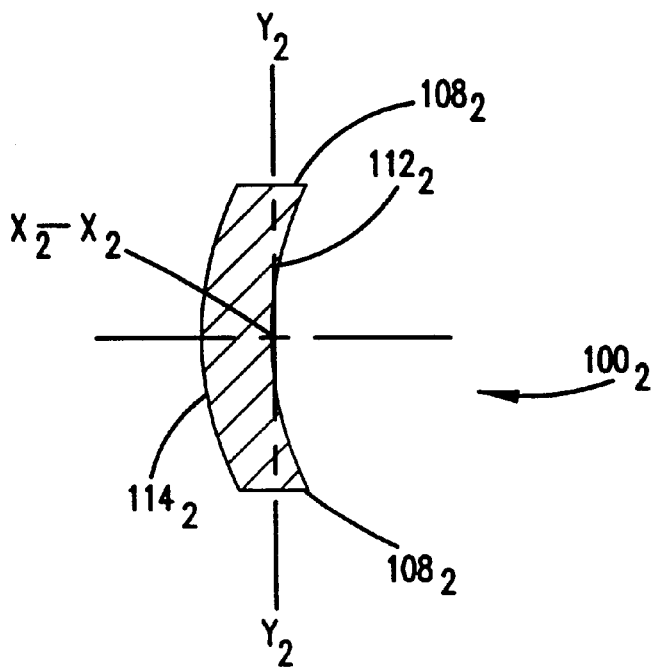
FIG. 8 is a view taken along line 8—8 of FIG. 7.

Referring now to the several drawing figures in which identical elements are numbered identically throughout, a description of the preferred embodiment of the present invention will now be provided. For purposes of illustrating the preferred embodiment, a description of the surgical procedure will be give with respect to an implant 10 such as that shown and described in commonly assigned U.S. Pat. No. 5,489,307. It will be appreciated that the present surgical procedures and apparatus can apply to a wide variety of implants including threaded implants such as those shown in U.S. Pat. Nos. 5,489,307 and 5,015,247, non-cylindrical implants such as those shown in U.S. Pat. No. 5,609,636 as well as conical implants for use in maintaining a desired lordosis. The term "implant" as used herein may also include bone implants as well as metallic implants.

The implant 10 (FIGS. 1–6) is a hollow cylinder 12 having male, square-profile threads 14 exposed on the exterior cylindrical surface of cylinder 12. The cylinder includes a forward interior chamber 16 and a rear interior chamber 17 separated by a reinforcing rib 19. A bond slurry or bone chips may be compacted into chambers 16,17.

A first plurality of holes 18 extend radially through the cylinder wall and communicate with the chambers 16,17. A second (and enlarged) plurality of holes 21 are disposed on diametrically opposed sides of the implant 10.

A rear end 22 of the implant has a slot 24 which communicates with the chamber 17. The slot 24 allows the bone slurry or bone chips to be impacted into the implant 10. A slot 25 is defined by rib 19. The slot 25 is sized to receive a distal end of a tool (as will be more fully described) to place the implant within a bore formed between opposing vertebrae. End caps (not shown) may be used with the implant. Such end caps are shown in U.S. Pat. No. 5,489,307.

In a preferred embodiment the technique of the present invention will be performed with a prescribed kit of tools. For the purpose of illustrating the preferred embodiment, the tools of the kit will now be described. It will be appreciated that the method of surgery can be practiced using a wide variety of tools of different size and shapes.

Each of the tools of a kit necessary to perform the surgery as described in this application will be separately described. The use of the tools will become apparent with the description of the method of the invention in Section IV.3 of this application. Unless otherwise specified, all tools are formed of stainless steel.

Since vertebrae size and disc space vary from patient-to-patient (and since such sizes vary along the length of the spine of any give patient), several sizes of implants 10 are anticipated. Presently, implants 10 having minor outside diameters ($D_m$) of 3 mm, 5 mm, 7 mm, 9 mm, 11 mm, 13 mm, 15 mm, 17 mm, 19 mm and 21 mm with lengths (L) of 10 mm, 12 mm, 14 mm, 16 mm, 18 mm, 20 mm, 24 mm, 28 mm, 30 mm, 32 mm, 34 mm, 38 mm, 42 mm and 44 mm, respectively, are anticipated to accommodate various spine locations and sizes. The major outside diameters ($D_M$) of the implants 10 are 2.5 mm larger than the minor outside diameters $D_m$.

Several of the tools to be described (e.g., a reaming tool 126) are sized for particular sizes of implants. Namely, the reaming tool 126 must form a bore sized to receive the implant. Since ten sizes of implants are anticipated, ten sizes of boring tools 126 are anticipated as will become apparent to one of ordinary skill in the art.

B. Centering Guide
1. Non-Lordotic Anterior

The present invention utilizes a novel centering guide to ensure accurate positioning of a drill tube prior to forming a bore and placing an implant. With initial reference to FIGS. 10–12, a centering guide 100 is shown for use in an anterior approach where a surgeon is approaching the disc space from an anterior side of the patient.

The centering guide $100_1$ is a rigid rod extending from a distal end $102_1$ to a proximal end $104_1$ along a longitudinal axis $X_1$—$X_1$. The distal end $102_1$ is rounded to facilitate easy insertion of the distal end $102_1$ into the disc space.

The anterior guide $100_1$ has, in cross section, a major transverse axis $Y_1$—$Y_1$ with the guide being symmetrical about the axis $Y_1$—$Y_1$ and axis $X_1$—$X_1$. At the distal end $102_1$, the guide $100_1$ has a distraction portion $106_1$. The distraction portion $106_1$ is defined by parallel and spaced-apart side edges $108_1$ which are spaced apart by a distance equal to desired distraction of the vertebrae.

The side edges $108_1$ act against the end plates of the opposing vertebrae to urge the vertebrae apart. The end plates hold the centering guide $100_1$ with the axis $X_1$—$X_1$ centrally positioned between the end plates. While the tool proximal end $104_1$ can be moved left or right relative to the vertebrae, the precise central positioning of the proximal end $104_1$ can be determined through x-ray analysis following placement of the centering guide $100_1$ such that a surgeon can be assured that the longitudinal axis $X_1$—$X_1$ extends perpendicular to a transverse plane of the vertebrae.

The distraction portion $106_1$ is provided with a plurality of indicia $110_1$ in the form of grooves positioned at 5 millimeter increments from the distal end $102_1$. The grooves $110_1$ are detectable in x-ray films to permit a surgeon to measure the degree of insertion of the distal end $102_1$ into a disc space. The guide $100_1$ includes a stop $109_1$ on edges $108_1$. The stop $109_1$ abuts vertebrae to prevent further insertion of guide $100_1$ beyond full insertion of portion $106_1$.

Extending between the side edges $108_1$ and extending the length from end $102_1$ to end $104_1$ are left and right (or first and second) guide surfaces $112_1$, $114_1$. The guide surfaces $112_1$, $114_1$ are concave and have a radius of curvature equal to a radius of curvature of a drill tube as will be described. While the preferred embodiment of the present invention will be described with reference to using a drill tube having a geometry which is complimentary to the guide surfaces $112_1$, $114_1$, it will be appreciated that the present invention could be performed without a drill tube and by using a drill, tap or other implement to facilitate insertion of an implant where the implement has a curved geometry to match the radius of curvature of the guide surfaces $112_1$, $114_1$ in which case the implement is directly guided by the guide surface, rather than being guided by an intermediate drill tube.

The proximal end $104_1$ is provided with a hole $105_1$ to permit a surgeon to place a tool (not shown) into the hole $105_1$ to twist the centering guide $100_1$ to release the centering guide $100_1$ if necessary. Also, an angled hole $107_1$ is provided near portion $106_1$ to permit insertion of a rod (not shown) into hole $107_1$ to permit a surgeon to force the guide $100_1$ to the mid-line of vertebrae. With the centering guide $100_1$ of FIG. 7 the end plates of the vertebrae will be distracted in parallel spaced apart relation since the side walls $108_1$ are parallel at the distraction portion $106_1$.

2. Non-Lordotic Posterior

FIGS. 7–9 show a centering guide $100_2$ similar to that of FIGS. 10–13 but differing due to the fact that centering guide $100_1$ of FIGS. 7–9 is intended for use in a posterior approach where a surgeon approaches the vertebrae from the posterior side of the patient. In the embodiments of FIGS. 7–18, simple elements are numbered similarly with the addition of subscripts to distinguish the embodiments.

Figure 12:
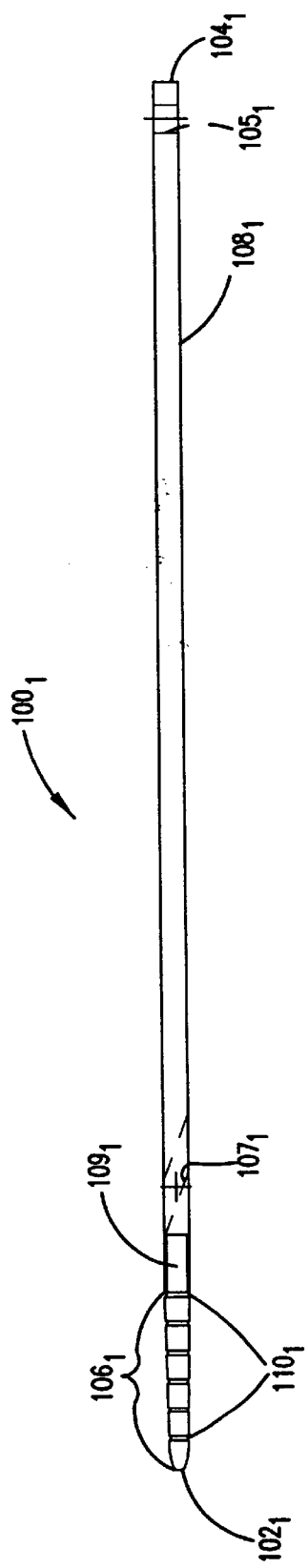
FIG. 12 is a top plan view of the centering guide of FIG. 10.
Figure 10:
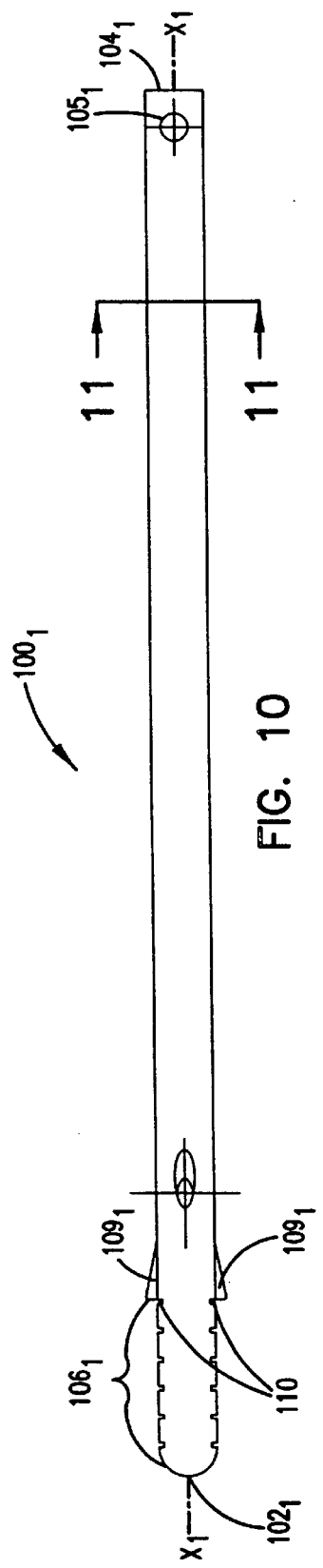
FIG. 10 is a side elevation view of a second embodiment of a centering guide according to the present invention for use in an anterior approach and without a lordotic distal end.
Figure 11:
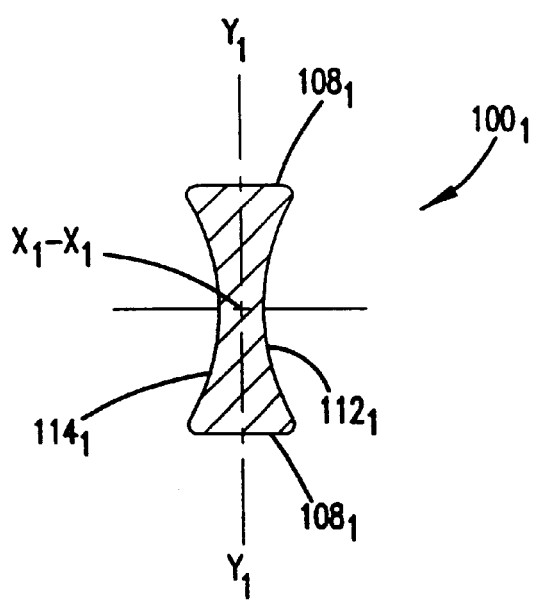
FIG. 11 is a view taken along line 11—11 of FIG. 10.

Like the centering guide $100_1$ of FIGS. 10–12, the centering guide $100_2$ of FIGS. 7–9 is for a non-lordotic parallel distraction appliance where the side edges $108_2$ are spaced apart in parallel alignment at the distraction portion $106_2$. Unlike the centering guide $100_1$ of FIGS. 10–12, the centering guide $100_2$ of FIGS. 7–9 is not symmetrical about its major transverse axis $Y_2$—$Y_2$ (although it is symmetrical about axis $X_2$—$X_2$. Instead, the centering guide $100_2$ of FIGS. 7–9 includes only a first concave guiding surface $112_2$ extending on one side of the centering guide $100_2$. The opposite surface $114_2$ is a convex surface to present a smooth surface opposing a dura following insertion of the centering guide $100_2$ as will be described.

3. Lordotic Posterior

The centering guides $100_1$,$100_2$ of FIGS. 7–12 both show distraction portions $106_1$,$106_2$ having distracting edges $108_1$,$108_2$ which are parallel and spaced apart. From time to time, it may be desirable to ensure that end plates of opposing vertebrae are retained at a desired degree of lordosis (i e., with a non-parallel angle between end plates of the opposing vertebrae).

Figure 17:
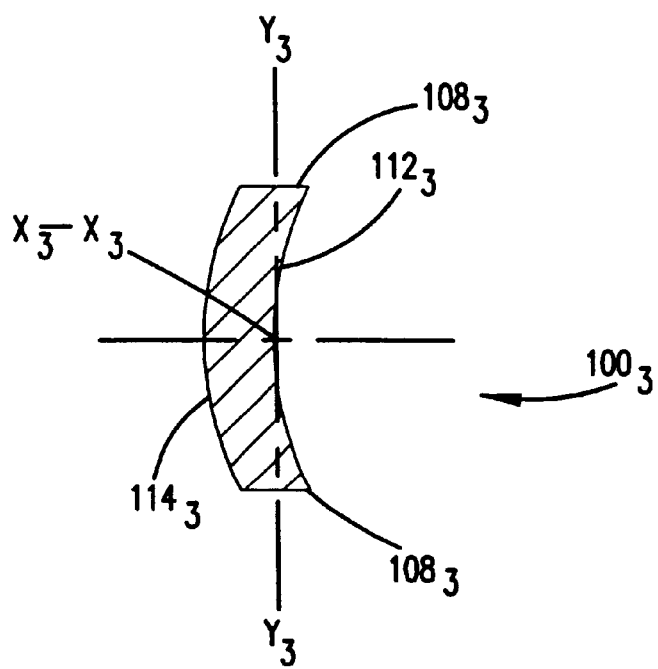
FIG. 17 is a view taken along line 17—17 of FIG. 16.

FIGS. 16–18 show a centering guide $100_3$ for a posterior approach and having a lordotic distraction portion $106_3$. The distraction portion $106_3$ has side edges $108_3$ placed at an angle, A, equal to the desired degree of lordosis. In all other respects, the centering guide $100_3$ of FIGS. 16–18 is identical to that of FIGS. 7–9.

4. Lordotic Anterior

Figure 14:
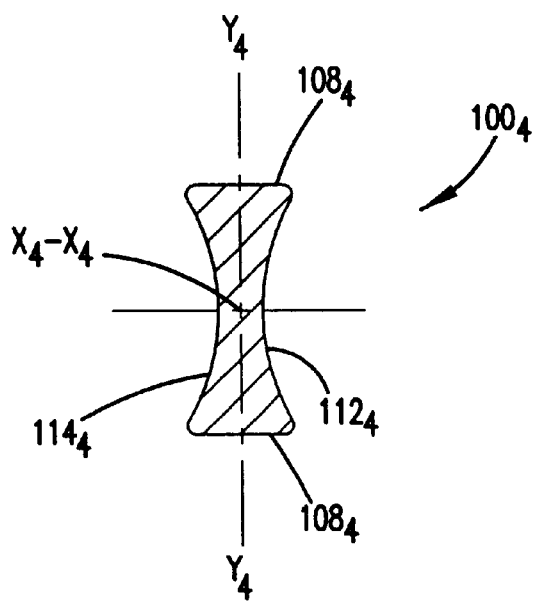
FIG. 14 is a view taken along line 14—14 of FIG. 13.

FIGS. 13–15 show a lordotic centering guide $100_4$ for use in an anterior approach. The distractor end $106_4$ of the tool $100_4$ has distracting side edges $108_4$ set at a lordotic angle, A', equal to but reverse that of the embodiment of FIGS. 16–18. In all other respects, the centering guide $100_4$ of FIGS. 13–15 is identical to that of FIGS. 10–12.

5. Laparoscopic

Laparoscopic versions of both the lordotic and non-lordotic centering guides can also be provided. Although not shown in the drawings, such laparoscopic centering guides would have a shorter length than the non-laparoscopic centering guides shown in the drawings. For example, a non-lordotic, laparoscopic anterior centering guide would be identical to that of guide $100_1$ (FIG. 10) but have its axial length detachable so that the terminal end $104_1$ is spaced from the distal tip $102_1$ by about 3 inches. After insertion of the portion $106_1$ into the disc space, approximately 1.5 inches of the guide surfaces $112_1$, $144_1$ would protrude beyond the vertebrae and provide a guide surface for directing a laparoscopic drill tube. The design would also permit the maintenance of insufflation.

C. Drill Tube

A drill tube 92 (FIGS. 20–22) is provided in the form of a hollow cylindrical tube 94. The distal end 96 of the tube 94 is provided with axially projecting teeth 98. The proximal end 99 of the tube 94 is flared outwardly. As will be apparent, ten sizes of tube 92 are required with inside diameters $D_{DT}$ to slip in close tolerance over ten sizes of implants 10 (i.e., $D_{DT}$ is 0.5 mm larger than $D_M$).

The teeth 98 each have a length, $T_L$, of preferably 3 mm. The valleys 97 are flat to provide stop surfaces to hit bone as teeth 98 are forced into vertebrae. This helps prevent the drill tube 92 from being forced too far into bone. The drill tube 92 is identical to that shown in U.S. Pat. No. 5,489,307.

An alternative embodiment of a drill tube 192 is illustrated in FIGS. 53–56. The drill tube is a hollow cylindrical tube 194 with an outside diameter having a radius of curvature to match the radius of curvature of the guide surfaces $112_1$, $114_1$. The distal end 196 of the tube 194 includes diametrically opposed and axially projecting sharpened teeth 198 for penetration into vertebrae. Diametrically opposed and axially extending retraction paddles 199 are provided ninety degrees offset from the teeth 198 (with reference to the longitudinal axis ($X'_D$—$X'_D$). The paddles 199 have a width (W in FIG. 54) equal to the desired distraction of the vertebrae. The proximal end 197 of the tube 194 is a handle to be gripped by a surgeon. The tube 194 has a length $L_D$ measured from the base of the teeth 198 and retraction paddles 199 to the base of the handle 197. The length $L_D$ is equal to the length of a centering guide (such as the length of guide $100_1$ of FIG. 10) between the proximal end $104_1$ and the insertion portion $106_1$. Therefore, when the insertion portion $106_1$ is fully inserted into the disc space, the end $104_1$ buts against the handle 197 when the teeth 198 are forced into the vertebrae.

D. Vertebral Reamer

A vertebral reamer 126 (or boring tool) (FIGS. 22 through 25), is provided for forming a bore. The reamer 126 is such as that shown in U.S. Pat. No. 5,489,307. The reamer 126 includes a shaft 128. A distal end of the shaft is provided with a reamer end 130 having side and end cutting blades 131. A proximal end of the shaft is provided with an outwardly flared hub 132. Extending from hub 132 is an axial shaft 134. For ten sizes of implants 10, ten sizes of reamers 126 are required with the kit. The outside diameter $D_R$ of reamer 126 equals the minor outside diameter $D_m$ of implants 10. The diameter $D_{RG}$ of the guide hub 133 equals the inner diameter of the drill tube $D_{DT}$.

E. Bone Tap

In the event a threaded implant is utilized (as is the case in the preferred embodiment of the present invention), the bores for the implants are partially pre-threaded. To pre-thread, a bone tap 142 (FIGS. 26–28) is provided, having a shaft 144. The top 142 is such as that shown in U.S. Pat. No. 5,489,307. At the distal end of the shaft 144 is a tapping head 146 having tapping threads 148. Near the proximal end of the shaft 144 is an enlarged diameter portion 156 having an outwardly flared flange 158. A handle 160 is secured to an enlarged portion 156. The shaft 144 is also enlarged at portion 162 adjacent tapping head 146. The enlarged portion 156 is sized with diameter $D_8$ to be received, in close tolerance, within the drill tube 92 such that the tube 92 will guide the tap 142 as will be more fully described.

Since ten sizes of implants 10 are intended to be utilized, ten sizes of bone taps 142 are required. Diameter $D_T$ is equal to the major outside diameter $D_M$ of implant 10. The head 146 has a minor outside diameter $D_t$ (i.e., the diameter without threads 148) equal to the minor outside diameter $D_m$ of the implants 10.

F. Implant Driver

To place implant 10, an implant driver 164 (FIGS. 29 through 33) is provided. The driver 164 is such as that shown in U.S. Pat. No. 5,487,307. A driver is also shown in U.S. Pat. No. 5,609,636. The driver 164 includes a shaft 166 having a reduced diameter distal portion 166a. A distal end of the shaft 166 is provided with a hub 168 sized to be received within slot 24 of the implant 10 to urge the implant 10 to rotate as the implant driver 164 is rotated. The implant driver 164 includes a stepped enlarged portion 170 including a first diameter portion 172, a second diameter portion 174 and a third diameter portion 176 to accommodate the different diameters of drill tubes 92. A handle 178 is secured to the shaft 164. Grooves 180,180a are formed on the shafts 166,166a and extend along their axial lengths. The grooves 180 provide a means for a surgeon to sight the alignment of the implant.

FIGS. 32–33 show the implant driver 164 with a collet 171. The collet 171 has a cylindrical, knurled body 173 slidably carried on shaft 166a. A pin 175 extending from body 173 into groove 180a permits collet 171 to slide on shaft 166 but not rotate. Four prongs 177 extend axially from body 173 toward hub 168.

Figure 46:
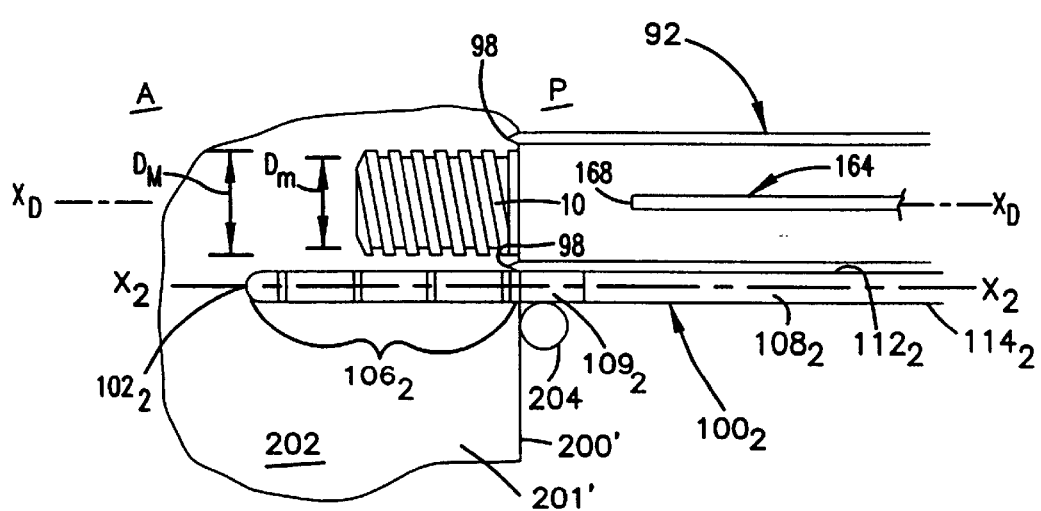
FIG. 46 is the view of FIG. 45 showing an implant inserted into the threaded bore of FIG. 45 and showing removal of the implant driving tool through the drill tube.

In use, shaft 166 is passed through end opening 24 of implant 10. Hub 168 is received within slot 25. The prongs 177 are forced by a surgeon pushing on body 171 for the prongs 177 to be urged between opposing surfaces of the implant 10 and shaft 166a to thereby securely capture the implant 10 on driver 164. As a result, the implant 10 cannot inadvertently fall off. (For ease of illustration, the Figures showing the method of the invention, e.g., FIG. 46, does not show use of collet 171).

G. Drill Tube Sheath

Drill tube 92 is passed through a patient's body to an implant site. To avoid risk of teeth 98 damaging vessels, nerves or organs, a drill tube sheath 300 is provided (FIGS. 34,35). The sheath 300 is such as that shown in U.S. Pat. No. 5,489,307. The sheath 300 is a hollow tube with inside diameter $D_S$ slightly smaller than the outside diameter of drill tube 92 (accordingly, ten sizes of sheath 300 are required). The sheath 300 has an axial slit 301 extending its entire length. The sheath 300 has a blunt distal end 302 and a flared proximal end 304.

The sheath is slipped onto the drill tube 92 with end 302 extending beyond the teeth 98. As the drill tube 92 is passed to an implant site the blunt end 302 covers the teeth and prevents the unwanted cutting of vessels, nerves or organs. When pressed against vertebrae, the end 302 abuts the vertebrae. With continued advancement of the tube 92 toward the vertebrae, the sheath 300 slides on the tube 92 until teeth 98 abut the vertebrae.

In the method of the invention, sheath 300 remains in place whenever drill tube 92 are used. However, for ease of illustration, sheath 300 is not shown in FIGS. 42–50.

H. Posterior Technique

The present invention will first be described with reference to use in a posterior approach. In a posterior approach, a surgeon seeks access to the spine through the back of the patient. Another alternative approach is the lateral approach, where the patient is on his side and a single cage is inserted across the disk space. An alternative approach is an anterior approach where the surgeon seeks access to the spine through the abdomen of a patient. The approaches can be done through open surgery or through laparoscopic surgery.

While a posterior approach will be described in detail, it will be appreciated that the present invention can be used in an anterior or lateral approach for both laparoscopic or non-laparoscopic procedures.

Figure 36:
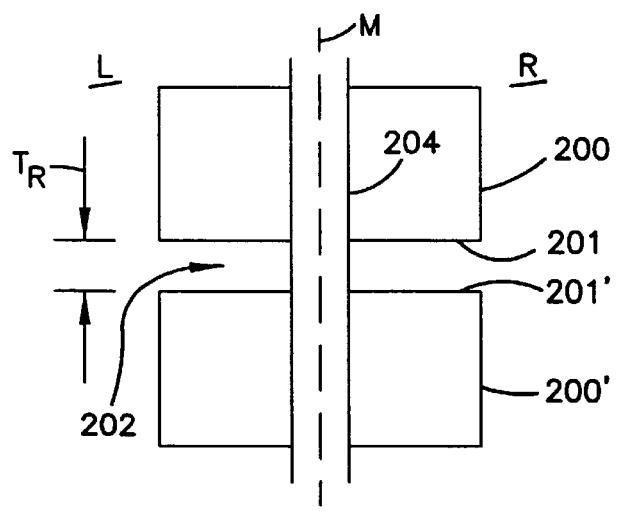
FIG. 36 is a schematic posterior to anterior view of two vertebrae separated by a disc space and showing a dura extending centrally along a mid line between the vertebrae.

With initial reference to FIG. 36, once a surgeon has identified two vertebrae 200,200' which are to be fused together, the surgeon identifies an implant 10 of desired size and the surgeon determines the desired amount of distraction of the disc space 202 to be required before placement of the implant 10. In selecting the implant size, the surgeon should ensure that the device will remain within the lateral borders of the intervertebral disc space 202 while also penetrating at least 3 mm into the vertebral bodies 200,200' cephalad and caudal to the disc.

In the posterior technique, a patient is placed on the operating table in either a prone or kneeling-sitting position. At the discretion of the surgeon, the spine is flexed slightly. Anesthesia is administered.

Exposure of the intervertebral disc is obtained through any suitable technique well-known in the art. The facet of the vertebrae is removed in as limited amount as possible to permit insertion of the instruments and the implants. Preferably, bone dissected from the lamina, facets and spinous process are preserved for later use as bone graft.

FIG. 36 shows two vertebrae 200,200' separated by a disc space 202. For ease of illustration, disc material is not shown in space 202 having an undistracted thickness $T_R$. In the posterior P to anterior A view, a dura 204 extends between the vertebrae 200,200' and is centrally positioned along a medial line, M, between the vertebrae 200,200'. The line M separates the disc space 202 and vertebrae 200,200' into a left side L and right side R corresponding to the patient's left and right sides.

Figure 37:
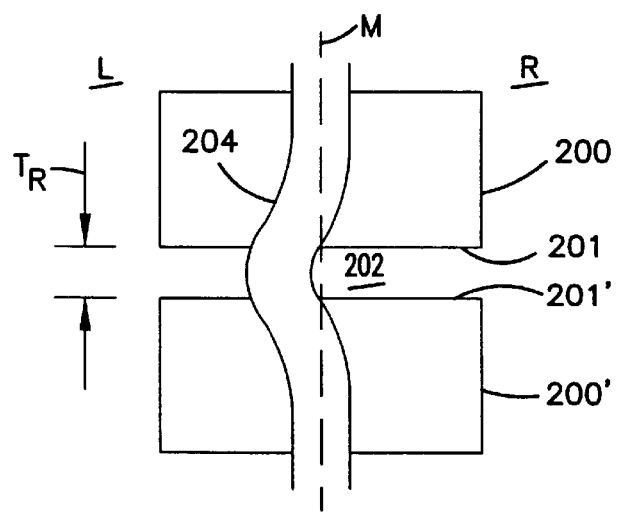
FIG. 37 is the view of FIG. 30 with a dura retracted to a left side.
Figure 38:
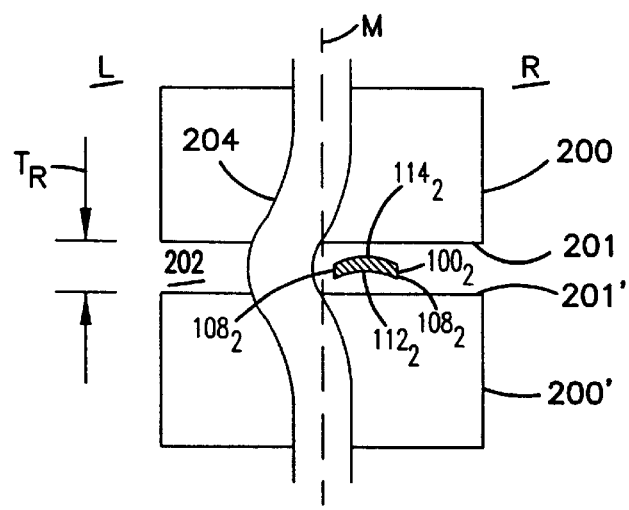
FIG. 38 is the view of FIG. 37 with a centering guide of the present invention such as that shown in FIG. 7 inserted into the disc space between the vertebrae prior to the centering guide being rotated to a distraction position.

As shown in FIG. 37, the dura 204 is first retracted to the left through any suitable means to expose the disc space 202 and vertebrae 200,200' at the medial line, M. A distal end $102_2$ of the centering guide $100_2$ of FIGS. 7–9 is inserted into the disc space 202 in the manner illustrated in FIG. 38 with the distracting side edges $108_2$ opposing and in line with the disc space 202.

Figure 39:
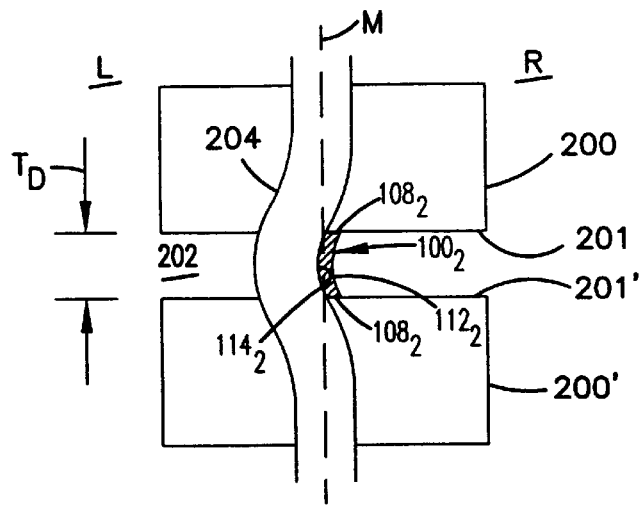
FIG. 39 is the view of FIG. 38 with the centering guide rotated to a distraction position.
Figure 40:
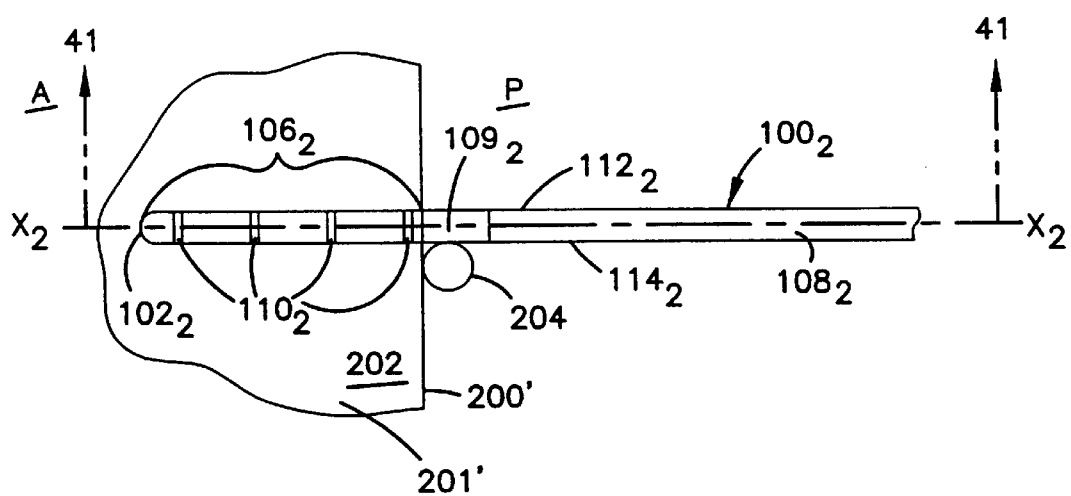
FIG. 40 is a plan view of a disc space showing the elements of FIG. 39.
Figure 41:
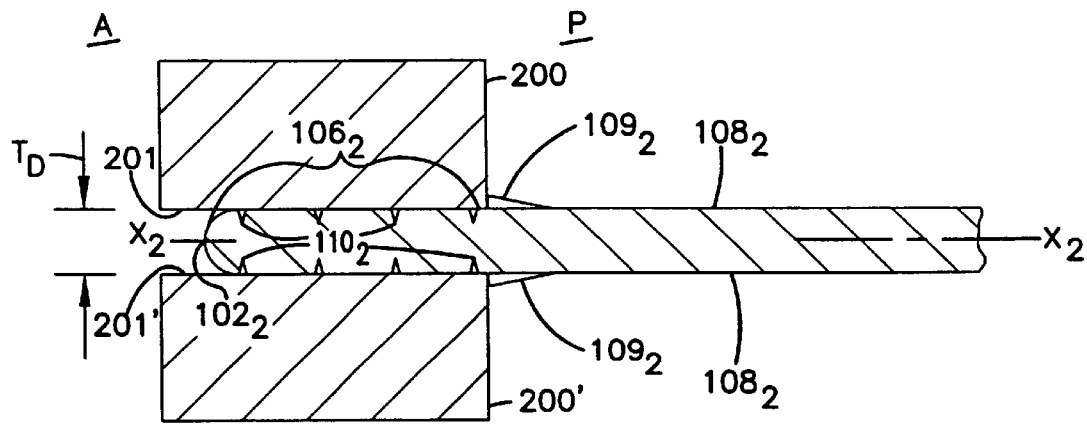
FIG. 41 is a view taken along line 41—41 of FIG. 40.
Figure 42:
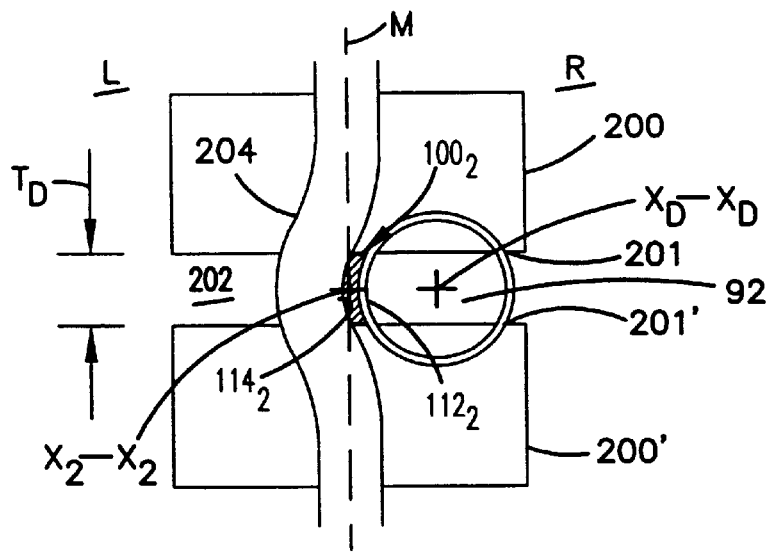
FIG. 42 is the view of FIG. 39 with a drill tube of FIG. 19 inserted into position and guided by the centering guide.
Figure 43:
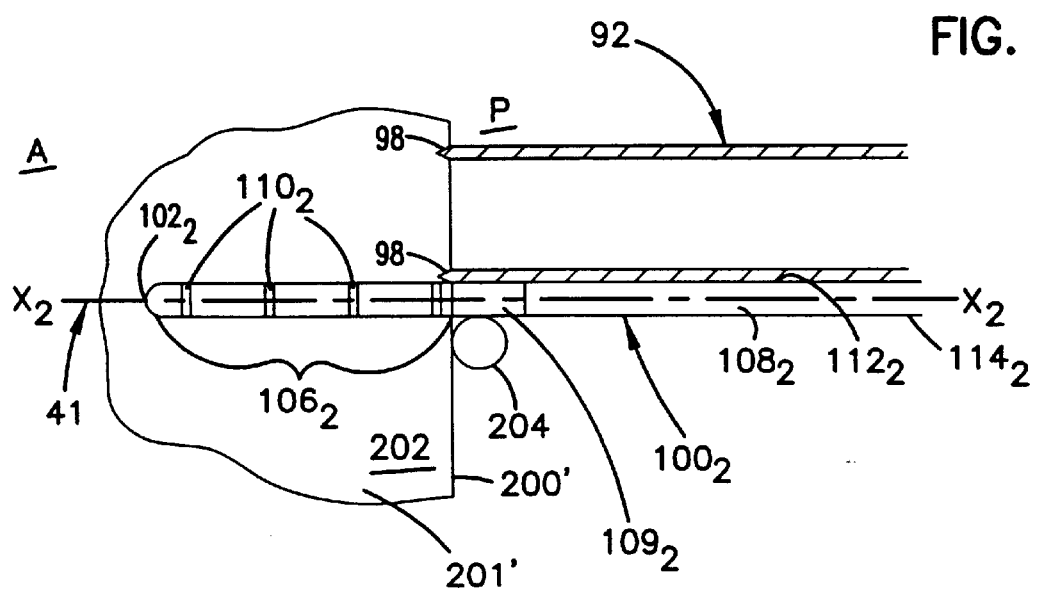
FIG. 43 is a plan view of the elements of FIG. 42 with the drill tube shown in section.

After initial insertion of the distal end $102_2$ into the disc space, the centering tool $100_2$ is rotated 90° to the position shown in FIG. 39 such that the side edges $108_2$ of the distraction portion $106_2$ oppose and distract the vertebrae and the convex surface $114_2$ is opposing the dura 204 to prevent damage to the dura 204. The vertebrae 200,200' are now distracted to a spacing of $T_D$ equal to the distance between side edges $108_2$.

The distraction portion $106_2$ of the guide $100_2$ is forced into the disc space 202 at the mid line M of the disc space 202. The size (i.e., the spacing between the side edges $108_2$) of the centering guide $100_2$ is selected to distract the annulus fibrosus without causing damage to the surrounding vertebral bone, annular fibers or spinal nerves. Accordingly, it is recommended that a surgeon initially insert a relatively narrow distal end centering guide (e.g., 6 millimeters) followed by successively larger guides until the annulus is distracted to the surgeon's satisfaction.

Once the correct maximum size distraction portion $106_2$ has been chosen, it is left in place. The disc space 202 has now been stretched so that a parallel distraction of the end plates 201,201' of the vertebrae 200,200' has occurred on both the left and right sides of the vertebrae. The distraction portion $106_2$ is fully inserted such that the indicia $110_2$ are flush or slightly recessed within the disc space.

Following placement of the distracting centering guide $100_2$, the drill tube 92 is placed against the centering guide $100_2$. Since the guiding surface $112_2$ of the centering guide $100_2$ is concave with a radius of curvature matching the outer radius of curvature of the drill tube 92, the drill tube 92 can be slid along the length of the guide $100_2$ into precise position with the axis $X_D$—$X_D$ of the drill tube 92 centrally positioned between the end plates 201,201' of the vertebrae 200,200'.

In a preferred embodiment, the drill tube 92 will be surrounded by a sliding protective sleeve 300 such as that shown in FIGS. 34–35 and described fully in U.S. Pat. No. 5,489,307. The thin wall of the drill sleeve 300 has substantially the same radius of curvature as the drill tube 92 and does not materially affect the positioning. At most, the addition of the protective sleeve 300 increases the spacing of the axis $X_D$—$X_D$ of the drill tube 92 from the axis $X_2$—$X_2$ of the guide $100_2$ (FIG. 51) but does not alter the central positioning of the axis $X_D$—$X_D$ of the drill tube 92 between the end plates 201,201'. For ease of illustration, the drill sleeve protective sleeve is not shown in FIGS. 42–50.

Figure 44:
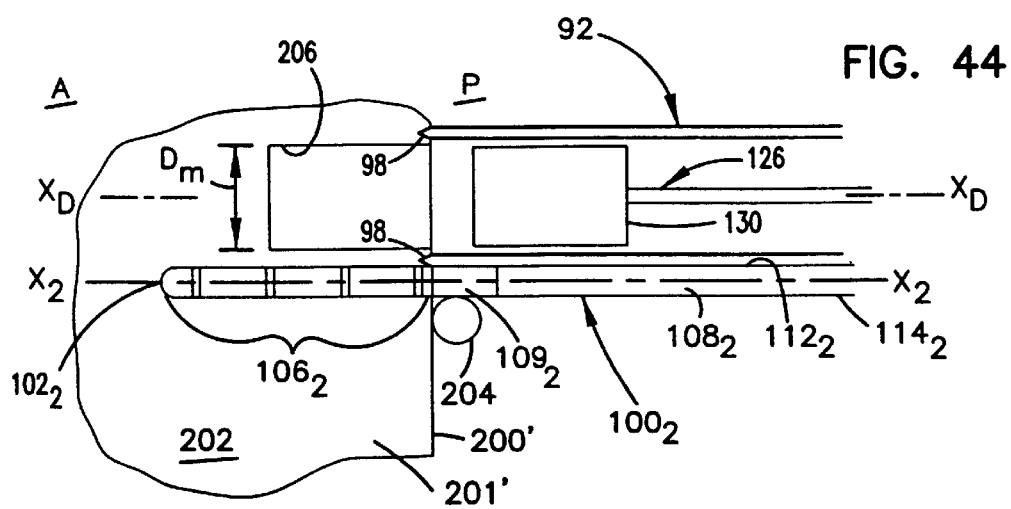
FIG. 44 is the view of FIG. 43 following formation of a bore in the disc space and vertebrae and showing retraction of a boring tool through the drill tube.

With the drill tube 92 in place, the preparation of the implant bore 206 is completed by inserting the reamer 126 into the drill tube 92 (FIG. 44). The reamer 126 is rotated with any suitable driver (such as driver 136 shown in U.S. Pat. No. 5,489,307).

Since the drill tube 92 is centrally placed with the axis $X_D$—$X_D$ of the drill tube 92 centrally positioned between the end plates 201,201', the reamer 126 will bore into the disc space 202 and bore equally into and through the end plates 201,201' of the opposing vertebrae. The reamer 126 is selected to form a bore 206 having a diameter $D_m$ equal to the minor outside diameter of the implant 10 (in the case of a cylindrical implant such as that shown in FIGS. 1–6).

Figure 45:
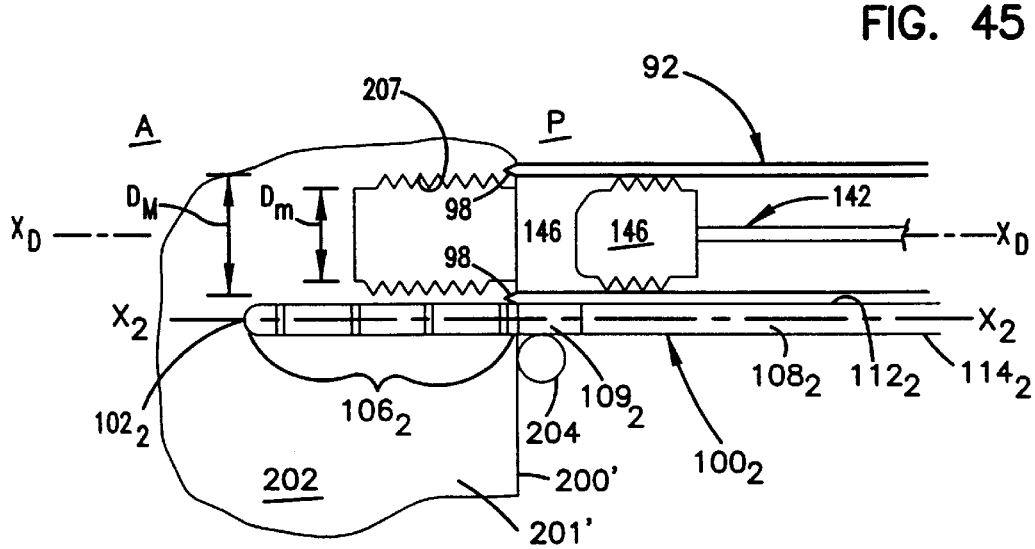
FIG. 45 is the view of FIG. 44 following formation of a tapped thread in the bore of FIG. 44 and showing removal of the tapping tool through the drill tube.

For use with a threaded implant 10 such as that shown in FIGS. 1–6, a bone tap 142 is passed through the drill tube 92 and rotated to at least partially pretap the bore (FIG. 45). The tap is then removed to expose a tapped bore 207 with the drill tube 92 remaining in place. The implant 10 may then be packed with a bone graft material. The graft may be autograft obtained previously from the iliac crest or some other graft material (e.g., allograft or artificial bone). The implant 10 is attached to the implant driver 164 by placing the hub 168 within the slot 25 and securing the implant 10 with the collet 171. The implant 10 is then passed through the drill tube 92. The implant 10 is threaded into the bore 207 with the implant driver 164 by the surgeon rotating the driver 164 and advancing it into the drill tube 92. As disclosed in U.S. Pat. No. 5,489,307, it is desirable that the larger holes of the implant are oriented in a superior-inferior direction (i.e., the larger holes are facing the vertebrae 200,200').

Figure 47:
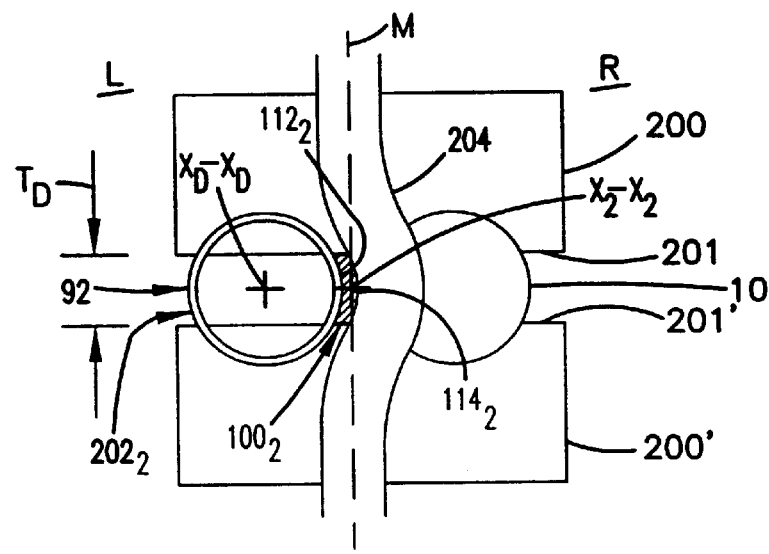
FIG. 47 is a posterior-to-anterior view showing a dura retracted to a right side over an inserted implant and with the centering guide reversed and with a drill tube positioned against the centering guide prior to formation of a bore on the left side of the vertebra.
Figure 48:
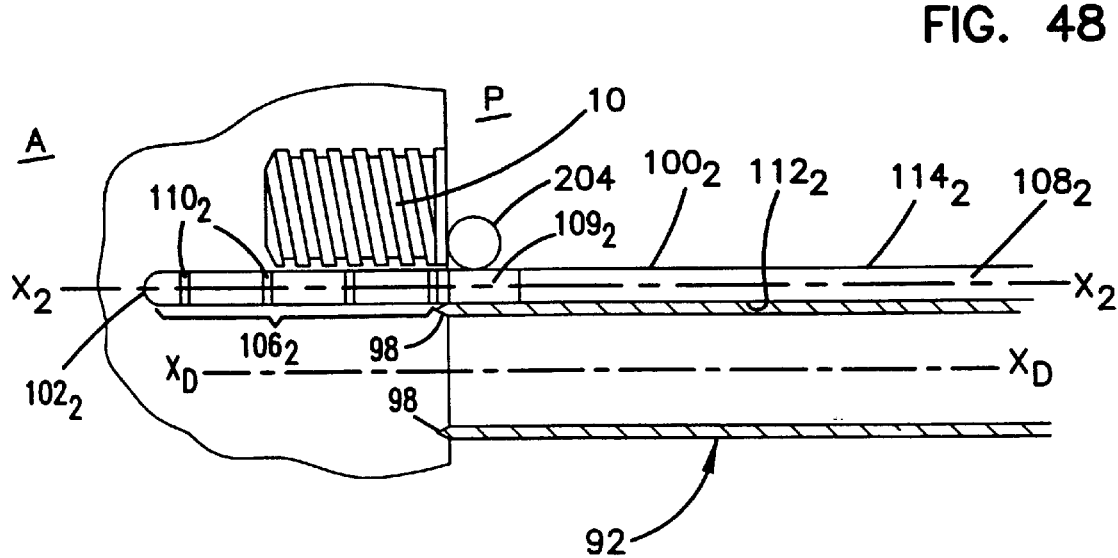
FIG. 48 is a plan view of the elements of FIG. 47 with the drill tube shown in section.
Figure 49:
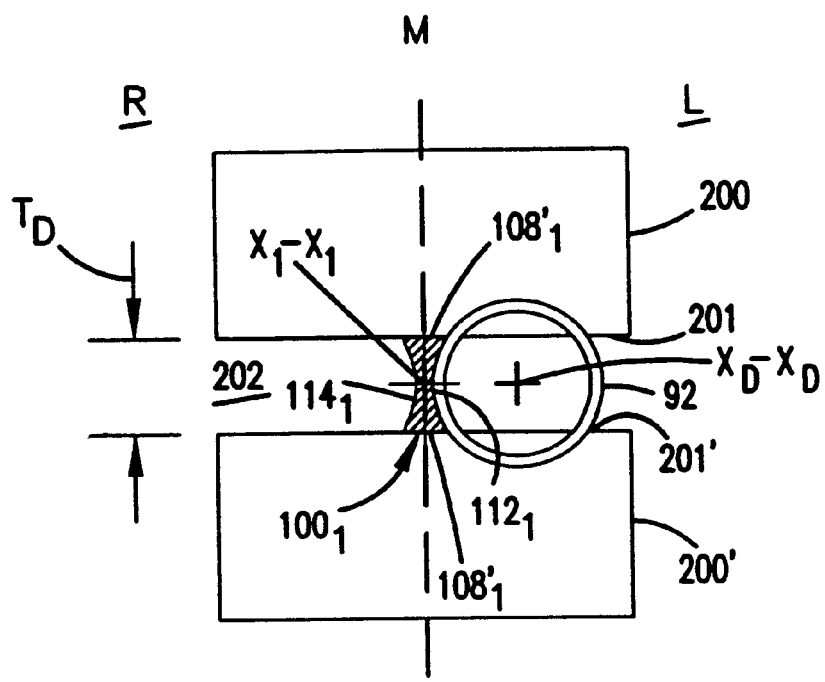
FIG. 49 is an anterior-to-posterior view of two vertebrae separated by a disc space and showing a non-lordotic, anterior approach centering guide of the present invention (such as that shown in FIG. 10) and shown inserted into the disc space between the vertebrae and with a drill tube being guided by the centering guide.

After the implant 10 is fully in place, the implant driver 164 is removed through the drill tube 92 (FIG. 47). The drill tube 92 is then removed. The dura 204 is retracted slightly and the centering guide 100 is then removed. The dura 204 is then retracted to the opposite side and the centering guide 100$_2$ is repositioned with the disc space 204 but rotated 180° relative to FIG. 39 so that the rounded side 114$_2$ is facing both the dura 204 and the previously placed implant 10 and the guide surface 112$_2$ is facing the opposite side of the disc space 202. The procedure can then be repeated by placing the drill tube 92 against the vertebrae with the drill tube 92 aligned by the guide 100$_2$ as previously described (FIG. 47).

I. Anterior Approach

The foregoing discussion illustrates the use and method of an apparatus of the invention in a posterior approach. It will be noted that for placing two implants 10, the centering guide 100$_2$ is removed and reinserted into the disc space 202 to reorient the guiding surface 112$_2$.

Figure 50:
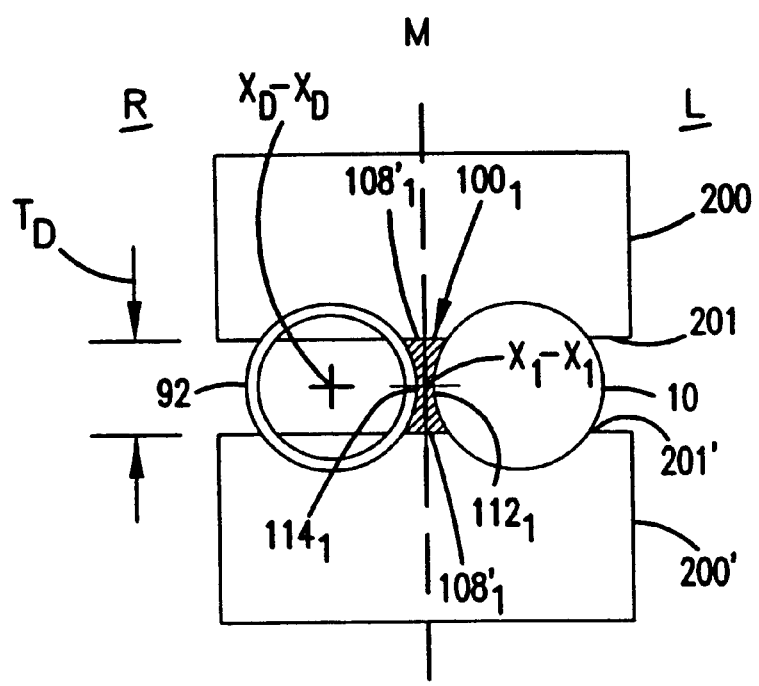
FIG. 50 is the view of FIG. 49 showing an implant inserted into a formed bore on a left side of the vertebrae and with the drill tube moved to be guided by an opposite side of the centering guide prior to formation of a bore on the right side of the vertebra.
Figure 51:
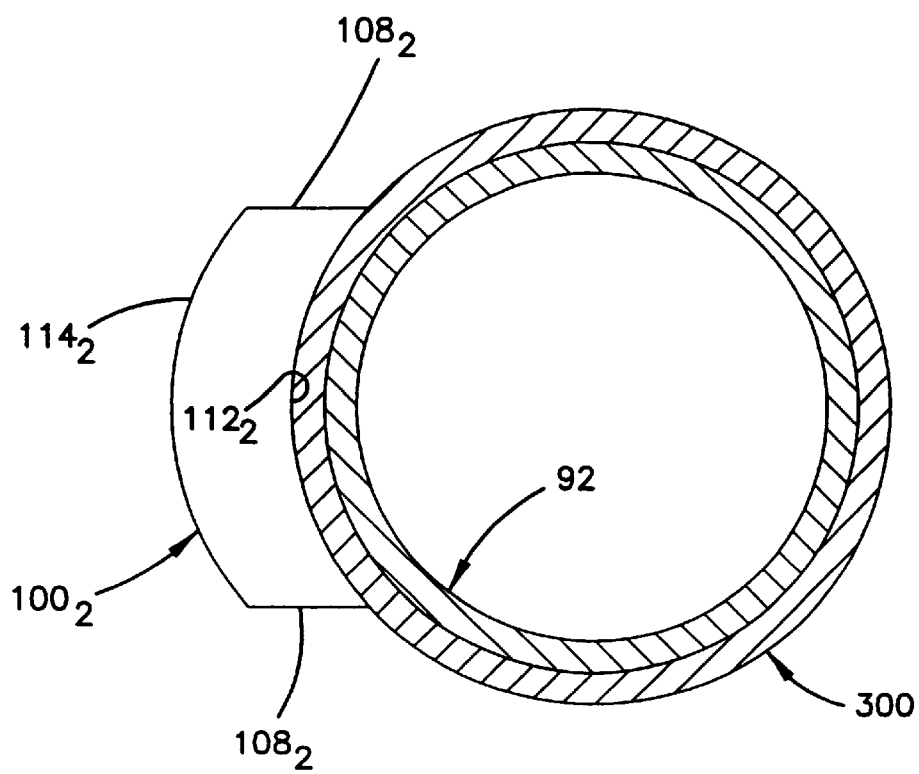
FIG. 51 shows a drill tube of FIG. 19 and a protective sleeve of FIG. 34 guided by a posterior centering guide of FIG. 7.
Figure 52:
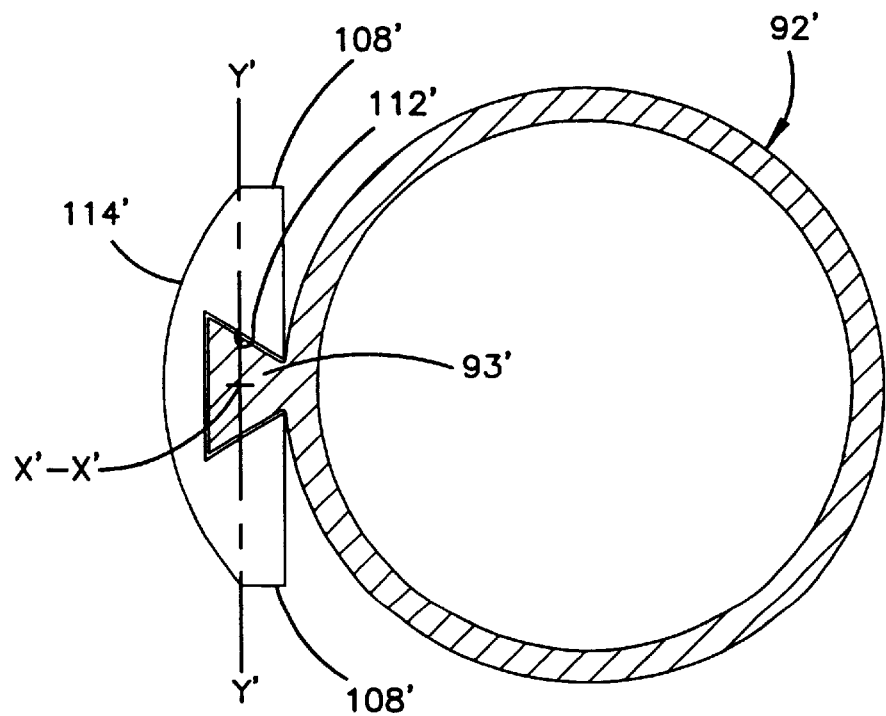
FIG. 52 shows a still further embodiment of a centering guide.

When performing an anterior approach, the surgeon uses the anterior guide 100,100$_4$ which has concave guiding surfaces 112,114 on opposite sides of the centering guide 100. With such structure, the anterior centering guide 100 is placed at the mid line M and a drill tube 92 is guided by a first 112 of the guiding surfaces 112,114 so that a first bore can be formed, tapped and an implant 10 inserted through the drill tube (FIG. 50). After the implant 10 is inserted, the centering guide 100 remains in place but the drill tube 92 is moved to the opposite side and guided into position by the second guiding surface 114 (FIG. 51). With the drill tube 92 in position on the second side, a bore 206 is then formed by passing the reamer and tap through the drill tube and a second implant is inserted through the drill tube.

J. Lateral Approach

The present invention is particularly suited for a lateral approach where an elongated single implant is to be placed in the inner vertebral space. The present invention requires smaller access space to the disc space which is of particular advantage in a lateral approach where there is substantial anatomic structure limiting access to the disc space in a lateral approach at certain vertebrae locations.

K. Additional Embodiments

In the foregoing description, the guide surface has been shown as a concave surface 112 having the same radius of curvature of the guided surface of the cylindrical drill tube. It will be appreciated that while a circular arc of a guide surface corresponding to a radius of curvature of a cylindrical drill tube is preferred, a plurality of complementary geometries could be used for the guide surface and the guiding surface.

In the present invention, if the surgeon were to place the drill tube 92 such that the axis $X_D$—$X_D$ of the drill tube 92 is not parallel to the longitudinal axis $X_2$—$X_2$ of the centering guide 100$_2$, such misalignment could be detected at the proximal end 104$_2$ of the guide 100$_2$ and be indicated by a spacing between the centering guide 100$_2$ and the drill tube 92. An alternative embodiment would be to provide a guiding surface on the centering guide which locks with a guided surface on the drill tube such that non-parallel alignment of the axis of the drill tube and the centering guide is not possible. For example, the guide surface 112' on the centering guide 100' could be dovetail grooved and the guided surface on the drill tube 92' could be a complementary shaped dovetail rail 93' which slides within the dovetail groove 112'. Such a modification would preclude non-parallel alignment of the axis $X_D'$—$X_D'$ of the drill tube 92' and the longitudinal axis X'—X' of the centering guide 100'. However, such a modification would require accurate alignment of the drill tube 92', whereas in the preferred embodiment previously disclosed, the drill tube 92 may be rotated about its axis $X_D$—$X_D$.

From the foregoing detailed description of the present invention it has been shown how the objects of the invention have been obtained in a preferred manner. However, modifications and equivalence of the disclosed concepts such as those which would occur to one of ordinary skill in the art are intended to be included within the scope of the present invention.

What is claimed is:

1. A method for implanting spinal fusion implants into a disc space between first and second vertebrae, the method comprising:

selecting a guide having first and second edges and having first and second sides therebetween, the first and second sides providing a spacing between the first and second edges a distance equal to a desired distraction of the first and second vertebrae, the guide being separable from a drill tube;

centrally positioning the guide into the disc space between the vertebrae such that the first edge is opposed to the first vertebrae and the second edge is opposed to the second vertebra;

forming a first implant bore between the first and second vertebrae adjacent the first side of the guide and forming a second implant bore between the first and second vertebrae adjacent the second side of the guide.

2. The method according to claim 1 performed through an anterior approach.

3. The method according to claim 1 wherein the first side and second side of the guide are concave.

4. The method according to claim 2 wherein the first edge and second edge define an angle to approximate a desired angle of lordosis between the first and second vertebrae.

5. The method according to claim 2 wherein the first implant bore is prepared by a drill passed through a separable drill tube.

6. The method according to claim 5 wherein the drill tube is maintained in a position for preparing the first implant bore by alignment with a portion of the guide.

7. The method according to claim 1 further comprising tapping the first implant bore and second implant bore to form threads within the implant bores.

8. The method according to claim 1 wherein the guide is configured to include a stop that abuts against the first and second vertebra to prevent insertion of the guide into the disc space beyond a predetermined distance.

9. The method according to claim 1 further comprising:

inserting a first spinal fusion implant into the first implant bore;

inserting a second spinal fusion implant into the second implant bore; and removing the guide from the disc space.

10. A method for implanting a spinal fusion implant into a disc space between a first vertebra and a second vertebra, the first vertebra having a first endplate, the second vertebra having a second endplate and each vertebra having a midline between a first lateral portion and a second lateral portion of the vertebra, the method comprising:

selecting a guide having first and second edges;

positioning the guide in the disc space between the vertebrae such that the first edge of the guide is urged against the midline of the first endplate and the second edge of the guide is urged against the midline of the second endplate of the second vertebra, no urging occurring in the disc space between the first and second lateral portions of the vertebrae;

forming a first implant bore in the first lateral portion of the first and second vertebrae; and forming a second implant bore in the second lateral portion of the first and second vertebrae.

11. The method according to claim 10 wherein the guide is configured to include a stop that abuts against the first and second vertebrae to prevent insertion of the guide into the disc space beyond a predetermined distance.

12. The method according to claim 10 wherein a distal portion of the guide is positioned in the disc space with the guide having a proximal portion extending along a longitudinal axis from the distal portion.

13. The method according to claim 12 wherein the guide is positioned between the disc space in a first orientation and the guide is rotated around the longitudinal axis to a second orientation to urge the first edge against the midline of the first endplate and urge the second edge against the second endplate.

14. The method according to claim 13 further comprising a step of placing an implement against the proximal portion of the centering guide, the implement having an external guided surface shape complementary to the proximal portion of the guide.

15. A method for performing a spinal stabilization procedure between adjacent first and second vertebrae of a vertebral column of a patient, the method comprising:

inserting a single guide into a central portion of a disc space between the adjacent first and second vertebrae;

forming a first implant bore between the first and second vertebrae adjacent a first side of the guide and forming a second implant bore between the first and second vertebrae adjacent a second side of the guide.

16. The method according the claim 15 wherein the guide is inserted through an anterior approach.

17. The method according to claim 15 wherein the guide includes a first and second edge having first and second sides therebetween, the first and second sides providing a spacing between the first and second edges a distance equal to a desired distraction of the first and second vertebrae.

18. The method according to claim 17 wherein the first edge and second edge define an angle to approximate a desired angle of lordosis between the first and second vertebrae.

19. The method according the claim 15 wherein the guide is configured to include a stop that abuts against the first and second vertebrae to prevent insertion of the guide into the disc space beyond a predetermined distance.

20. The method according to claim 15 further including a step of removing the guide.

* * * * *